US006955877B1

(12) United States Patent
Nygren et al.

(10) Patent No.: US 6,955,877 B1
(45) Date of Patent: Oct. 18, 2005

(54) IN VITRO SELECTION AND OPTIONAL IDENTIFICATION OF POLYPEPTIDES USING SOLID SUPPORT CARRIERS

(75) Inventors: Per-Ake Nygren, Ekero (SE); Mathias Uhlen, Taby (SE); Olof Nord, Stockholm (SE)

(73) Assignee: Affibody AB, Bromma (SE)

( * ) Notice: Subject to any disclaimer, the term of this patent is extended or adjusted under 35 U.S.C. 154(b) by 342 days.

(21) Appl. No.: 10/031,910

(22) PCT Filed: Jul. 20, 2000

(86) PCT No.: PCT/GB00/02809

§ 371 (c)(1),
(2), (4) Date: Jul. 31, 2002

(87) PCT Pub. No.: WO01/05808

PCT Pub. Date: Jan. 25, 2001

(30) Foreign Application Priority Data

Jul. 20, 1999 (GB) .................................. 9917027

(51) Int. Cl.$^7$ ............................................. C07K 1/00
(52) U.S. Cl. ........................... 435/6; 435/7.1; 435/68.1
(58) Field of Search ........................... 435/6, 7.1, 69.1, 435/91.1, 92.1, 68.1; 532/23.1, 23.4

(56) References Cited

FOREIGN PATENT DOCUMENTS

| WO | WO 98/54312 | * 12/1998 | .......... C12N 15/10 |
|---|---|---|---|
| WO | WO 98/54312 A | 12/1998 | |
| WO | WO 99/02671 | 1/1999 | .......... C12N 15/10 |
| WO | WO 99/35293 A | 7/1999 | |

OTHER PUBLICATIONS

Clackson, T and Wells, J A: Trends in Biotechnology, vol. 12, pp. 173-184 (1994).
Smith, G P and Petrenko, V A: American Chemical Society, vol. 97, pp. 391-410 (1997).
Mattheakis, L C et al: An in vitro polysome display system for identifying ligands from very large peptide libraries; Proceedings, The National Academy of Sciences of The USA, vol. 91, pp. 9022-9026 (Sep. 1994).
Hanes, J et al: Comparison of *Escherichia coli* and rabbit reticulocyte ribosome display systems; Federation of European Biochemical Societies, Letters 450, pp. 105-110 (1999).

Roberts, R W and Szostak, J W: RNA-peptide fusion for the *in vitro* selection of peptides and proteins, Proceedings, The National Academy of Sciences of The USA, vol. 94, pp. 12297-12302 (Nov. 1997).
Lutz, J et al: Current Opinion in Biotechnology, vol. 9, pp. 534-548 (1998).
Roberts, R W: Current Opinion in Chemical Biology, vol. 3, pp. 268-273 (1999).
Nord, K et al: Protein Engineering, vol. 8, Issue 6, pp. 601-608 (1995).
Nord, K et al: Nature Biotechnology, vol. 15, pp. 772-777 (Aug. 1997).
Rüther, U: Nucleic Acids Research, vol. 10, No. 19, pp. 5765-5772 (1982).
Nygren, P-Å et al: Journal of Molecular Recognition, vol. 1, No. 2, pp. 69-74 (1988).
Carothers, A M et al: Biotechniques, vol. 7, No. 5, pp. 494-499 (1989).
Savolainen, P et al: Society for Molecular Biology and Evolution, vol. 17, No. 4, pp. 474-488 (2000).
Hopman, A H N et al: The Journal of Histochemistry and Cytochemistry, vol. 46, No. 6, pp. 771-777 (1998).
Larsson, M et al: Protein Expression and Purification, vol. 7, pp. 447-457 (1996).
Nilsson, B et al: Protein Engineering, vol. 1, No. 2, pp. 107-113 (1987).
Gunneriusson, E et al: Applied and Enviromental Microbiology, vol. 65, No. 9, pp. 4134-4140 (Sep. 1999).
Tawfick, D S and Griffiths, A D: Nature Biotechnology, vol. 16,pp. 652-656 (Jul., 1998).
Hanes, J and Plückthun, A: *In vitro* selection and evolution of functional proteins by using ribosome display; Proceedings, The National Academy of Sciences of the USA, vol. 94, pp. 4937-4942 (May, 1997).
Doi, N and Yanagawa, H: Federation of European Biochemical Societies, Letters 475, pp. 227-230 (1999).

* cited by examiner

*Primary Examiner*—Kenneth R. Horlick
*Assistant Examiner*—Heather G. Calamita
(74) *Attorney, Agent, or Firm*—Todd E. Garabedian; Wiggin and Dana LLP

(57) ABSTRACT

A method for the selection of one or more desired polypeptides includes cell free expression of nucleic acid molecules immobilized on a solid support system to produce polypeptides. The solid support carrying system is for biospecific interaction with at least the desired polypeptide or a molecule attached thereto. The method also includes separation of the solid support carrying both the desired polypeptide and the nucleic acid encoding it. Finally, the method optionally includes recovery of the nucleic acid and/or the desired polypeptide, and molecular libraries for use in these methods.

11 Claims, 20 Drawing Sheets

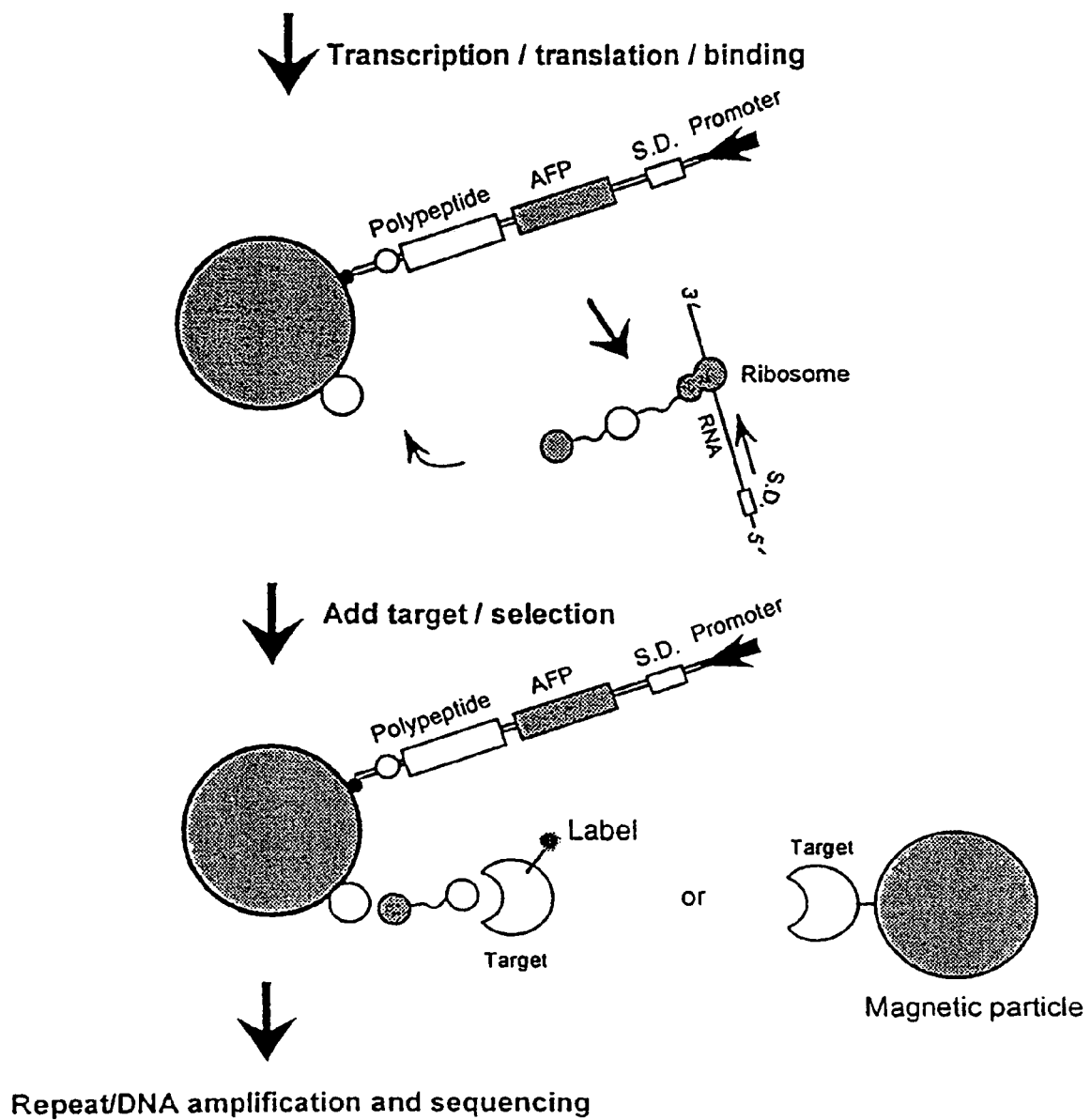
FIG. 2CONT'D

Immobilized RNA/Target added

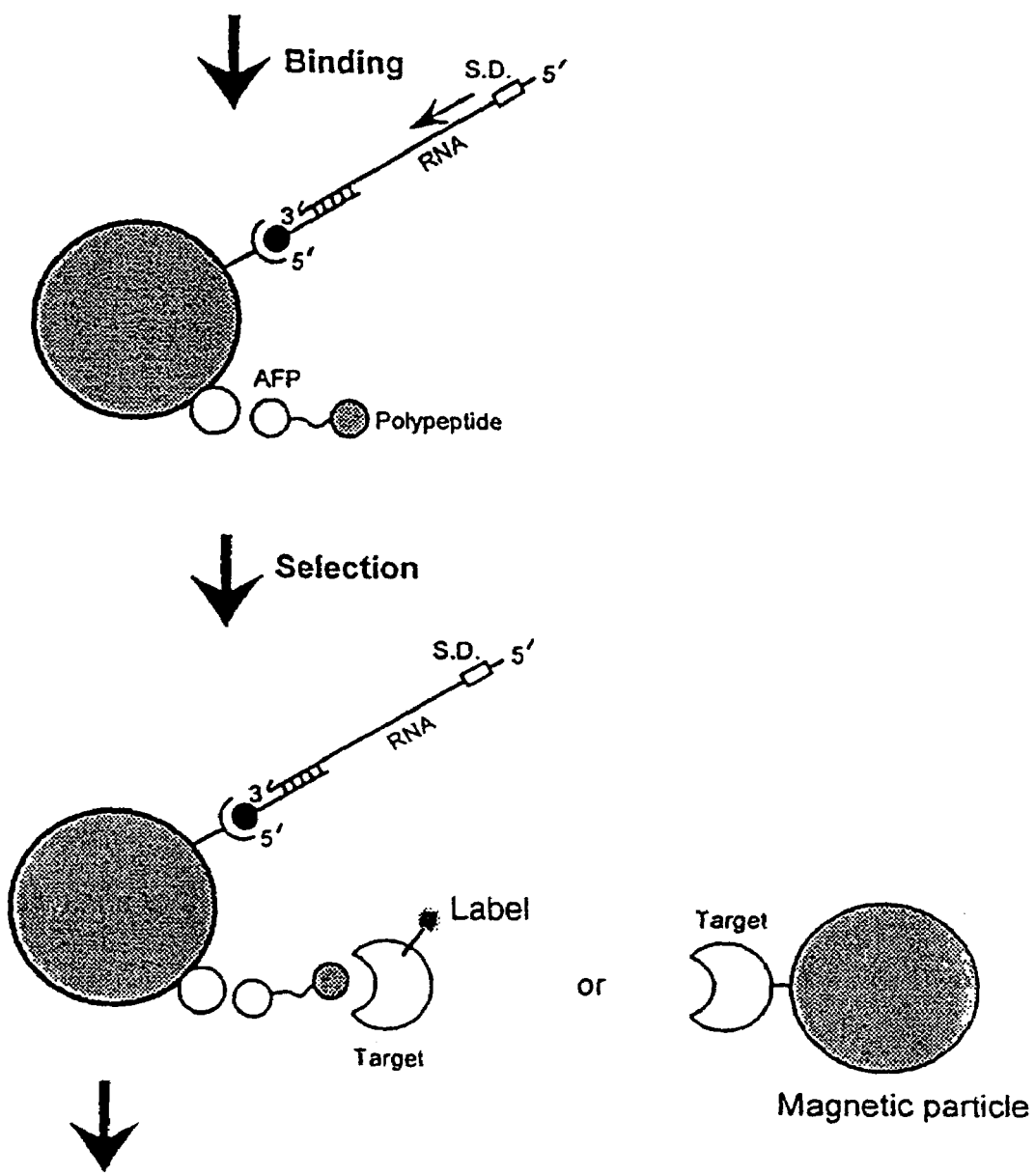
Reverse transcribe RNA / PCR amplification and sequencing
FIG. 3CONT'D Reverse transcribe RNA / PCR amplification and sequencing

A

B

IN VITRO SELECTION AND OPTIONAL IDENTIFICATION OF POLYPEPTIDES USING SOLID SUPPORT CARRIERS

BACKGROUND OF THE INVENTION

1. Field of the Invention

This invention provides methodology for in vitro selection and, if desired, subsequent identification of proteins or peptides with desired properties from pools of protein or peptide variants (libraries).

2. Discussion of the Related Art

Proteins and peptides, hereinafter jointly referred to as polypeptides, with desired properties such as binding affinity to a particular target molecule, catalytic activity, chemical or enzymatic activity or immunogenic activity are of great importance in many areas of biotechnology such as drug and vaccine development, diagnostic applications and bioseparation.

Recent progress in gene technology has provided the introduction of novel principles of isolating and identifying such polypeptides from large collections of variants constructed by different methods including combinatorial principles (Clackson and Wells, *Trends Biotechnol.* 12, pp. 173–184 [1994]). Typically, using biosynthesis for production of the library members, large pools of genes are constructed, encoding the individual library members, allowing for later selection or enrichment of desired variants using an appropriate bait molecule or chemical condition (Smith and Petrenko, *Chem. Rev.* 97, pp. 391–410 [1997]). For identification of selected variants, several techniques have been described to provide a physical link between the translated protein (phenotype) and the genetic information encoding it (genotype), allowing for identification of selected library members using DNA sequencing technology.

Using phage or cell display technologies, a genotype-phenotype coupling is obtained through incorporation of the individual library members into the coat or cell surface structures respectively of phage or cells containing the corresponding gene, which is typically inserted into phage, phagemid, plasmid or viral DNA. In the construction of such libraries, the gene pools need to be transformed into a recipient cell used for biosynthesis of the corresponding proteins. The practical limitations associated with this critical step to obtain large (complex) libraries (typically above $10^9$ different members) have been a driving force for the development of alternative technologies based on in vitro transcription and translation of genetic information, thereby avoiding the transformation step.

Examples of such technologies are ribosomal display (Mattheakis et al., *Proc. Natl. Acad. Sci. USA* 91, pp. 9022–9026 [1994]; Hanes et al., *FEBS Letters* 450, pp. 105–110 [1999]) and RNA-peptide fusions using puromycin (Roberts and Szostak, *Proc. Natl. Acad. Sci. USA* 94, pp. 12297–12302 [1997]). In ribosomal display, a gene pool (typically polymerase chain reaction (PCR) products containing signals necessary for transcription and translation) is transcribed in vitro to produce a corresponding pool of mRNA used for ribosome mediated translation of proteins which typically, through the absence of translational stop signals, remain physically linked to the ribosome-mRNA complex. This allows for selection of polypeptides on the basis of the characteristics of the same and identification through DNA sequencing after conversion of the ribosome-associated mRNA into DNA by the use of reverse transcriptase. However, special precautions (temperature, buffer conditions) must be taken to ensure the stability of the ribosome-mRNA-protein complexes, limiting the conditions under which selection can be performed (Jermutus et al., *Curr. Opin. Biotechnol.* 9, pp. 534–548 [1998]; Hanes et al., op. cit. [1999]). In the RNA-peptide fusion system, puromycin-tagged RNA is used during translation, resulting in covalent RNA-protein/peptide links via acceptance by the ribosome of puromycin in the nascent polypeptide chain. However, new puromycin-mRNA fusions have to be prepared for each round of selection, severely limiting the efficiency of the technology (Jermutus et al., op. cit. [1998]; Roberts, *Curr. Opin. Chem. Biol.* 3, pp. 268–273 [1999]).

A further system has been described by Tawfik and Griffiths (Nature Biotechnology, (1998) 16; 652–656) which is cell free but seeks to mimic the effect of cells in creating compartments to link genotype and phenotype. Micelles are formed using a water-in-oil emulsion which can then be broking by mixing with ether. However, this system is not without problems, the two phase system results in several practical limitations. In order to recover the encapsulated molecules, the two phase system must be broken which is rather laborious, requiring several washes and causing a loss of material. Furthermore, the non-water components necessary to create the two-phase system might inhibit or denature biomolecules and the encapsulation itself makes it more difficult to deliver additional reagents necessary for e.g. detection or capture of specific molecular entities.

OBJECTS AND SUMMARY OF THE INVENTION

The present invention is based on the finding that by using a solid support such as a particle system as carrier of genetic information (e.g. RNA or DNA) used for identification and having coupled thereto the corresponding in vitro translated polypeptide, methodology linking genotype and phenotype is established. Isolation of solid support particles carrying a desired library member or members may typically be performed using sorting technology employing e.g. fluorescent labels incorporated into a target molecule or the library polypeptide members or by magnetic isolation using magnetic particles containing an immobilized target molecule.

Thus according to one aspect of the present invention there is provided a method for the selection of one or more desired polypeptides comprising:
  (a) cell free expression of nucleic acid molecules immobilized on a solid support system to produce polypeptides, the solid support carrying means for biospecific interaction with at least the desired polypeptide or a molecule attached thereto;
  (b) separation of the solid support carrying both the desired polypeptide and the nucleic acid encoding it; and optionally
  (c) recovery of the said nucleic acid and/or said desired polypeptide, preferably of the nucleic acid.

The selection method of the invention can be considered also as a method of enriching the desired polypeptide from a starting library of molecules containing it. 'Enrichment' referring to increasing the relative proportion of the desired polypeptide within the sample of variant molecules. Similarly, the method can be considered one by which a nucleic acid molecule of interest, i.e. which encodes the desired polypeptide is enriched.

Step (a) is cell free. The term "cell" is used in a broad sense to include cell and preferably cell-like systems and thus preferably encompasses liposomes, micelles formed by water-in-oil emulsions, gels, glass or any other multi-phase system which creates a physical barrier between one gene expression/biospecific interaction system and another. According to a preferred aspect of the present method, no actual compartmentalisation takes place, no membrane or other separation system is required to isolate individual nucleic acid molecules from one another.

The separation step (b) may advantageously be effected by interaction of the immobilized desired polypeptide with a target (e.g. biospecific) reactant therefor which carries means permitting separation of the resulting solid support/nucleic acid/desired polypeptide/target reactant complex. Such means may, for example, comprise a label such as a fluorescence label or a magnetic particle. In this way the complex may be separated using fluorescence-activated cell sorting (FACS) technology or magnetic separation technology.

The immobilized nucleic acids may, for example, be RNA or DNA encoding individual polypeptides such as the members of a protein library. It will be appreciated that their in vitro translation will be effected in combination with or following in vitro transcription in the case of immobilised DNA.

Suitable solid supports for use in the present invention may be any of the well known supports or matrices which are currently widely used or proposed for immobilisation, separation etc. These may take the form of particles, sheets, gels, filters, membranes, fibres, capillaries, or microtitre strips, tubes, plates or wells etc., particulate solid supports being preferred. Conveniently the support may be made of glass, silica, latex or a polymeric material.

Non-magnetic polymer beads suitable for use in the method of the invention are available from Dyno Particles AS (Lillestrøm, Norway) as well as from Qiagen, Pharmacia and Serotec. However, to aid manipulation and separation, magnetic beads are preferred. The term "magnetic" as used herein means that the support is capable of having a magnetic moment imparted to it when placed in a magnetic field, and thus is displaceable under the action of that field.

Thus, using the method of the invention, after gene expression and biospecific interaction the magnetic particles may be removed onto a suitable surface by application of a magnetic field eg. using a permanent magnet. It is usually sufficient to apply a magnet to the side of the vessel containing the sample mixture to aggregate the particles to the wall of the vessel and to pour away the remainder of the sample.

Especially preferred are superparamagnetic particles for example the well-known magnetic particles sold by Dynal AS (Oslo, Norway) as DYNABEADS, are suited to use in the present invention.

Methods for attachment of nucleic acid molecules or proteinaceous moieties such as the cognate binding partners or target molecules discussed herein to a solid support are well known in the art and many include but are not limited to chemical coupling, e.g. involving amine, aldehyde, thiol, thioether or carboxyl grous or biospecific coupling for example taking advantage of interactions between streptavidin and biotin or analogues thereof, IgG and protein A or G, HSA and protein G, glutathione S-transferase (G-ST) and glutathione, maltose and maltose binding protein, antibody and antigen (including proteins, peptides, carbohydrates and haptens), lectins and carbohydrates, hisidines and chelating groups and nucleic acid/nucleic acid hybridization.

The expressed polypeptides may advantageously be fusion proteins containing an affinity fusion partner, the solid support carrying a cognate binding partner for said affinity fusion partner as the means for biospecific interaction. Thus the expressed fusion protein will typically comprise an affinity fusion partner portion as well as the desired polypeptide or a molecular variant of the desired polypeptide from the library of molecules which contains the desired polypeptide. In this way a library of fusions proteins is generated having a variable portion which is made up of the desired polypeptide or variants thereof from the starting library and an essentially common portion, the affinity fusion partner. As appropriate, reference is made herein to molecular libraries which may be libraries of nucleic acid molecules or libraries of polypeptides. Likewise, a library member may refer to a polypeptide or a nucleic acid molecule.

In an alternative embodiment a target molecule capable of biospecific interaction with the desired polypeptide is immobilized on the solid support as the means for biospecific interaction. In this embodiment, a library of fusion proteins may also be generated, each fusion protein incorporating a reporter protein which may conveniently be used in the separation step (b) as well as the desired polypeptide or a molecular variant of the desired polypeptide from the library of molecules which contains the desired polypeptide. Thus again, the motif of a variable portion and an essentially common portion (here the reporter protein) is provided. Each molecule within the library of fusion proteins will thus preferably have a region which is essentially the same as the corresponding region of other molecules in the library, while the variable region of each library member will differ from all or at least most of the corresponding regions of the other library members. In general one variable region will not differ significantly from some or all of the other variable regions within the library of fusion proteins. In this way the impact of minor variations in primary amino acid sequence on e.g. binding can be investigated.

Recovery of the nucleic acid(s) encoding the desired polypeptide(s) may, for example, be effected by in vitro amplification, e.g. by means of PCR, reverse transcriptase PCR or rolling circle amplification.

The sequence of separated and/or amplified nucleic acid (s) may be determined, e.g. by conventional sequencing techniques, thereby permitting determination of the sequence of the desired polypeptide in order to identify it.

In a further aspect of the invention the starting pool of nucleic acids encoding individual library members may be of considerable complexity (e.g. $\geq 10^{15}$ members)(Roberts, op. cit. [1999]). The number of different nucleic acid species immobilized per solid phase carrier particle may be controlled in the preparation of the particles, for example through use of different concentrations of the molecule serving as anchor (for example DNA, RNA, PNA or a protein) or through pretreatment of particles with competing material. Thus the selection of discrete particles in only a single selection procedure according to the invention may result in simultaneous selection of a significantly reduced number of library members.

Performance of repeated cycles in accordance with the invention, optionally employing solid phase support particles with successively decreasing numbers of nucleic acid anchoring sites, and optionally with simultaneous dilution of the nucleic acid material, may result in gradual convergence to a limited set of library members which may be subjected to individual analysis at a clonal level in order to identify a desired polypeptide species. Where selection technology such as FACS is employed, use of different threshold values for positive selection may permit stringent selection of solid phase carrier particles containing high numbers of the desired library member.

Alternatively, after a reduction in the number of library members by separation in accordance with the invention, the enriched pool of nucleic acid sequences may be subjected to further selections using a different selection principle, such as (but not limited to) cell display, phage display, plasmid display, ribosomal display or mRNA-peptide fusions.

Thus, the method of the invention is preferably an iterative process with enrichment of the polypeptide(s) of interest occurring as more cycles are performed. While there may be some diffusion of expressed polypeptides and binding to neighbouring beads (or regions of solid support, particles etc.), local binding to the polypeptide's own bead (or region of solid support, particle etc.) will be preferred. Thus after several cycles significant enrichment will be achieved. Method steps (a) and (b) will thus preferably be performed more than once, typically the number of cycles will be between 1 and 100, prefeably 2 to 50, more preferably 2 to 20, e.g. 5 to 10. In this way the number of variants may be very significantly limited and the relatively small number remaining can be analysed one-by-one, e.g. by ELISA, statistical analysis of clones after sequencing or Biacore analysis.

In another aspect of the invention, the selection of a solid phase support carrier carrying multiple nucleic acid species, including the desired library member, may be used to produce useful reagents without the need for identification of the particular desired library member. Thus the method may be performed in an iterative manner but stopped when the selected sample still contains a mixed population of DNA molecules; this pool of DNA fragments can be used as a "polyclonal" material, not defined at the molecular level but still useful.

In a further embodiment of the invention two different nucleic acid libraries may be immobilized on separate solid support systems and the method may be used to select and identify interacting pairs of polypeptides. Thus, for example, one of the nucleic acid libraries may encode polypeptides such as antibodies, antibody fragments, peptides or protein domains and the other may encode cDNA encoded polypeptides.

According to a further aspect of the invention is provided a molecular library comprising a solid support system having immobilised thereon a plurality of nucleic acid molecules and associated with each of said nucleic acid molecules and also immobilised on said support system means for biospecific interaction with the expression product of one or more of said nucleic acid molecules.

The solid support system is preferably particulate and thus each particle will conveniently carry one nucleic acid molecule from the library and means for biospecific interaction with the expression product thereof. Thus the aforementioned 'association' between nucleic acid molecules and means for biospecific interaction is achieved. As discussed in more detail above, the library of nucleic acid molecules will conveniently encode fusion proteins and the means for biospecific interaction may interact, typically bind, to either the variable or common portion of said fusion protein.

BRIEF DESCRIPTION OF THE DRAWINGS

In the accompanying drawings, which serve to illustrate the invention without in any way limiting it.

After washing, the solid support carrier particles are incubated with labelled target molecules, e.g. comprising fluoroscein isothiocyanate (FITC), allowing physical isolation of fluorescent-positive particles, for example by FACS or by magnetic separation. Thus, particles carrying complexes between the labelled target and the particle-associated library member gene product and its genetic information (DNA) are isolated.

Using e.g. PCR, the DNA fragments coupled to individual or multiple isolated particles or beads are re-amplified and used for identification of the selected polypeptide(s) or optionally consecutive rounds of particle immobilization, in vitro transcription and translation followed by selection, e.g. by FACS.

Figure 3:
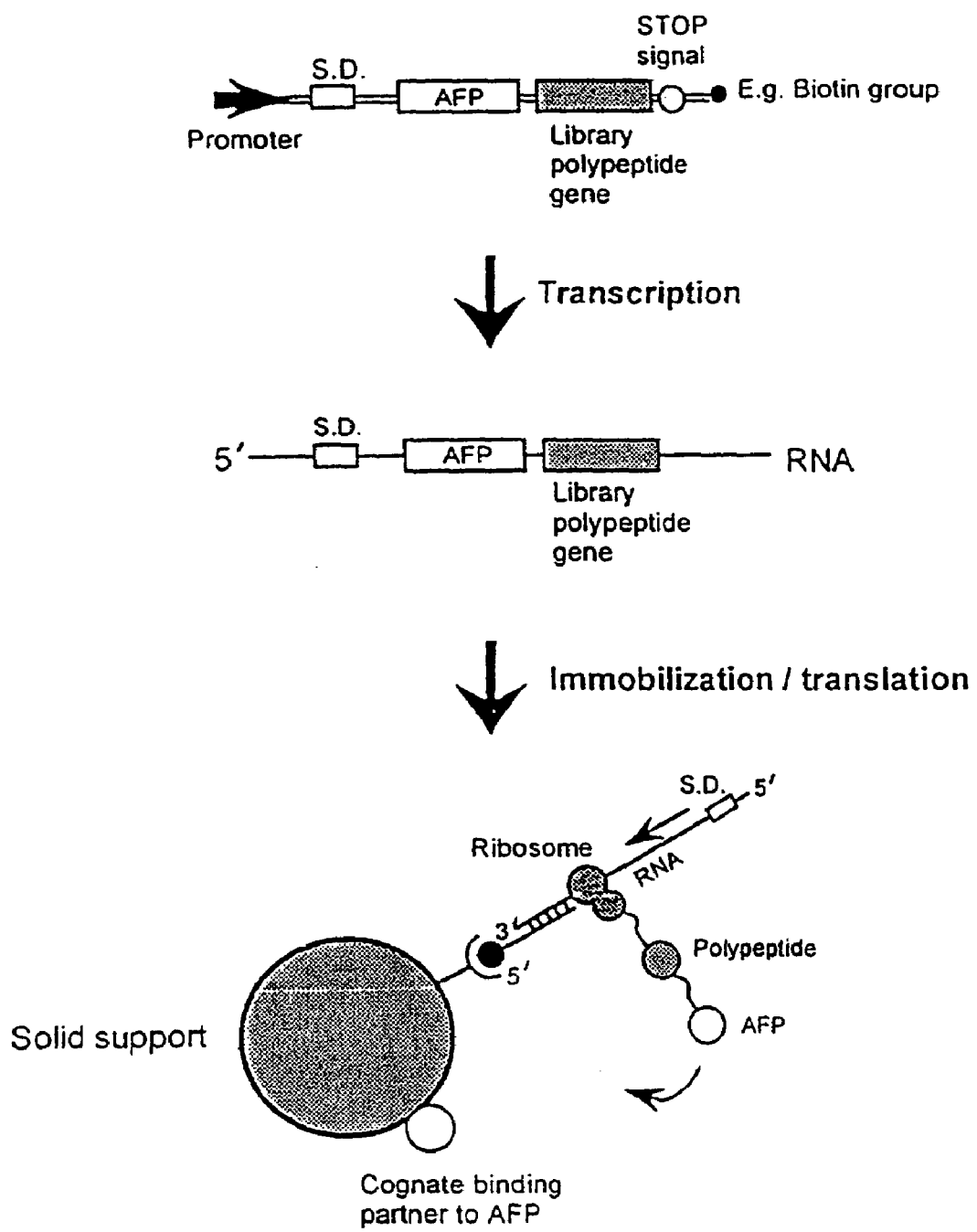

FIG. 3 is a schematic representation of the use of a solid support as carrier of coupled genetic and protein information (immobilized mRNA/labelled target in solution version). From a library of genetic constructs containing signals necessary for library member transcription and protein translation, RNA (mRNA) is produced (transcription) in vitro and immobilized onto particles of a suitable carrier support (e.g. via hybridization between complementary sequences present in the mRNA and immobilized DNA, PNA or RNA fragments). The immobilized mRNA molecules encode individual library members as genetically fused to a common affinity fusion partner (AFP) for which the cognate binding partner (CBP) is immobilized onto the particles (e.g. via streptavidin/biotin chemistry). After addition of components for in vitro translation (e.g. an *Escherichia coli* S30 extract), the mRNA molecules are translated to produce the different protein library members. Through interaction between the immobilized binding partner and the newly translated affinity fusion partner, the individual library members are physically linked to the solid support carrier particles containing the genetic information (mRNA) encoding them.

After washing, the solid support carrier particles are incubated with labelled target molecules, e.g. comprising FITC, allowing physical isolation of fluorescent-positive particles, e.g. by FACS. Thus, individual or multiple particles carrying complexes between the labelled target and the particle-associated library member gene product and its genetic information (mRNA) are isolated.

Using e.g. reverse transcriptase PCR, the bead/particle-associated mRNA molecules are converted into the corresponding DNA fragments which are PCR amplified and used for identification of the selected polypeptide(s) or optionally consecutive rounds of in vitro transcription, particle immobilization, in vitro translation followed by selection, e.g. by FACS or magnetic selection.

Figure 4:
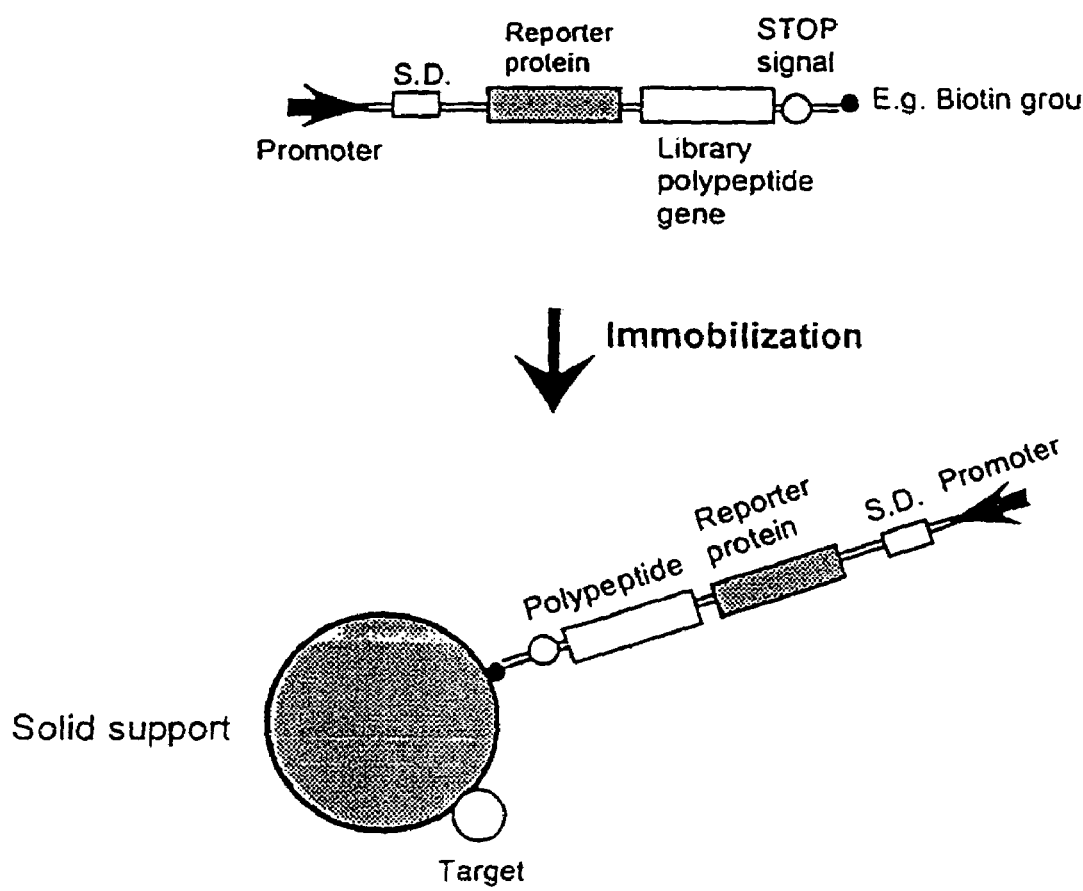
Figure 4:
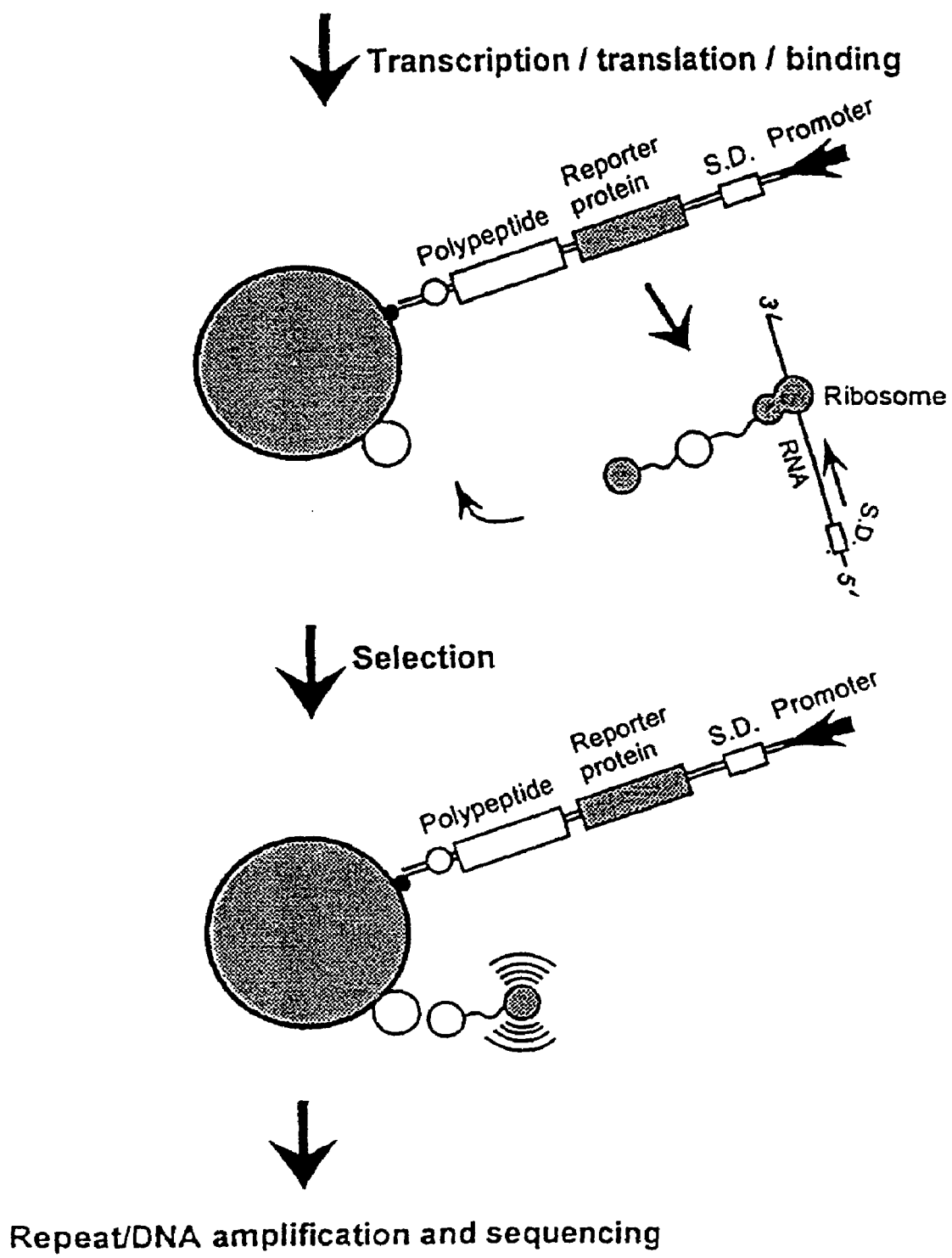

FIG. 4 is a schematic representation of the use of a solid support as carrier of coupled genetic and protein information (immobilized DNA/labelled binder version). A library of DNA construct (typically but not exclusively PCR fragments) containing signals necessary for library member RNA transcription and protein translation is immobilized onto discrete particles of a suitable carrier support (e.g. using biotin/streptavidin chemistry by incorporation of a biotin group into the DNA of the primer used for the PCR amplification and the use of streptavidin coated beads). The particles also carry the target molecule with which interacting library members are desired to interact. This immobilization can be achieved using e.g. standard coupling chemistries such as EDC/NHS chemistry or biotin/streptavidin chemistry. The genetic constructs encode individual library members as genetically fused to a reporter fusion partner (RFP) such as an enzyme or autofluorescent protein such as green fluorescent protein (GFP). After addition of components for in vitro transcription and translation (e.g. an *Escherichia coli* S30 extract), RNA (mRNA) molecules are produced which encode for the subsequently translated different protein library members. Through interaction between the immobilized target molecule and the newly translated library member, individual library members capable of interaction with the solid support immobilized target molecule are physically linked to the solid support carrier particles containing the genetic information (DNA) encoding them.

After washing, the solid support carrier particles are sorted, e.g. using FACS technology or magnetic separation, to isolate individual or multiple particles carrying complexes between the immobilized labelled target and the particle-associated library member gene product. Thus, particles carrying complexes between the labelled target and the particle-associated library member gene product and its genetic information (DNA) are isolated.

Using PCR, the DNA fragments coupled to discrete isolated beads are re-amplified and used for identification of the selected polypeptide(s) or optionally consecutive rounds of particle immobilization, in vitro transcription and translation followed by separation, e.g. by FACS or magnetic selection.

Figure 5:
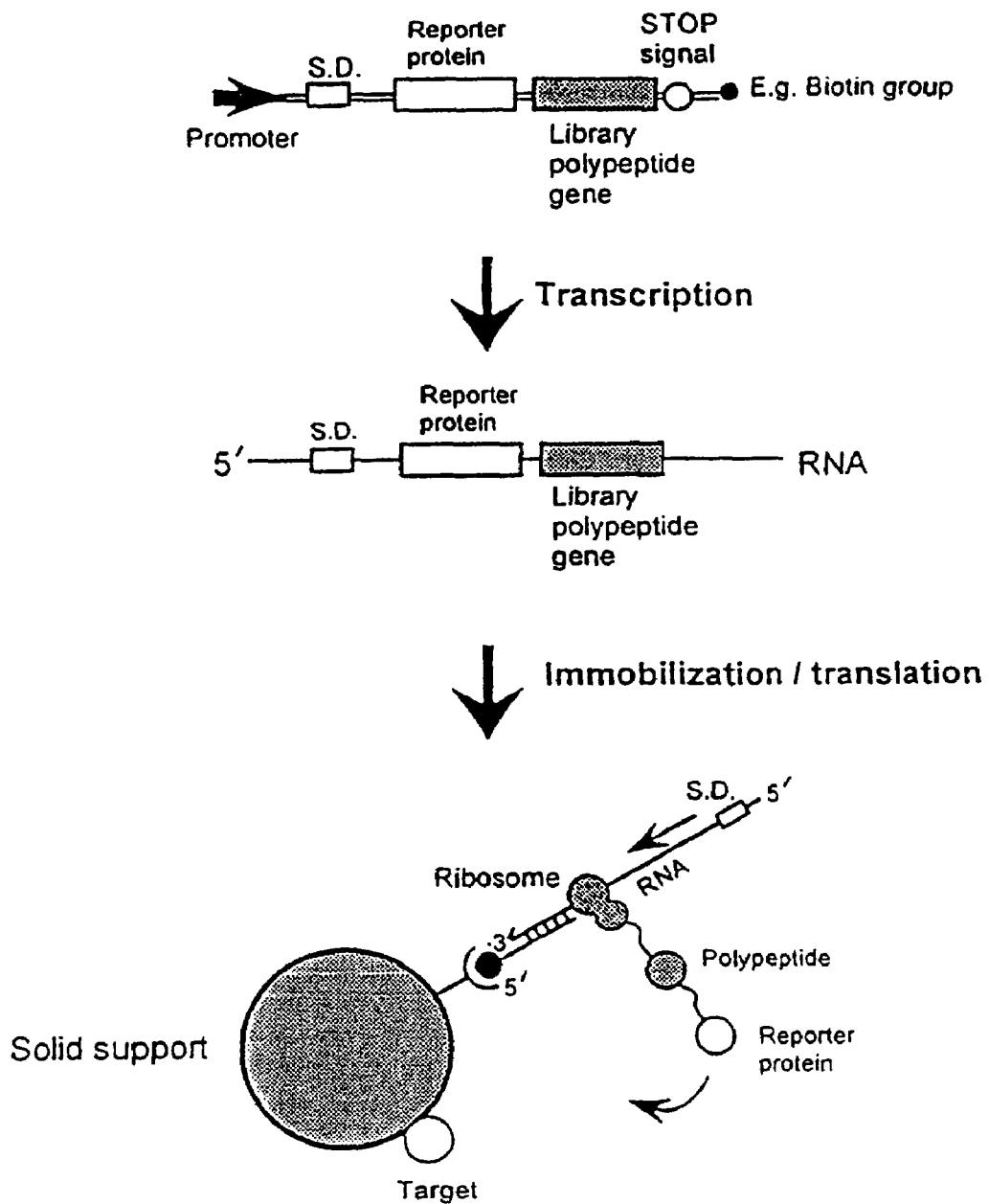
Figure 5:
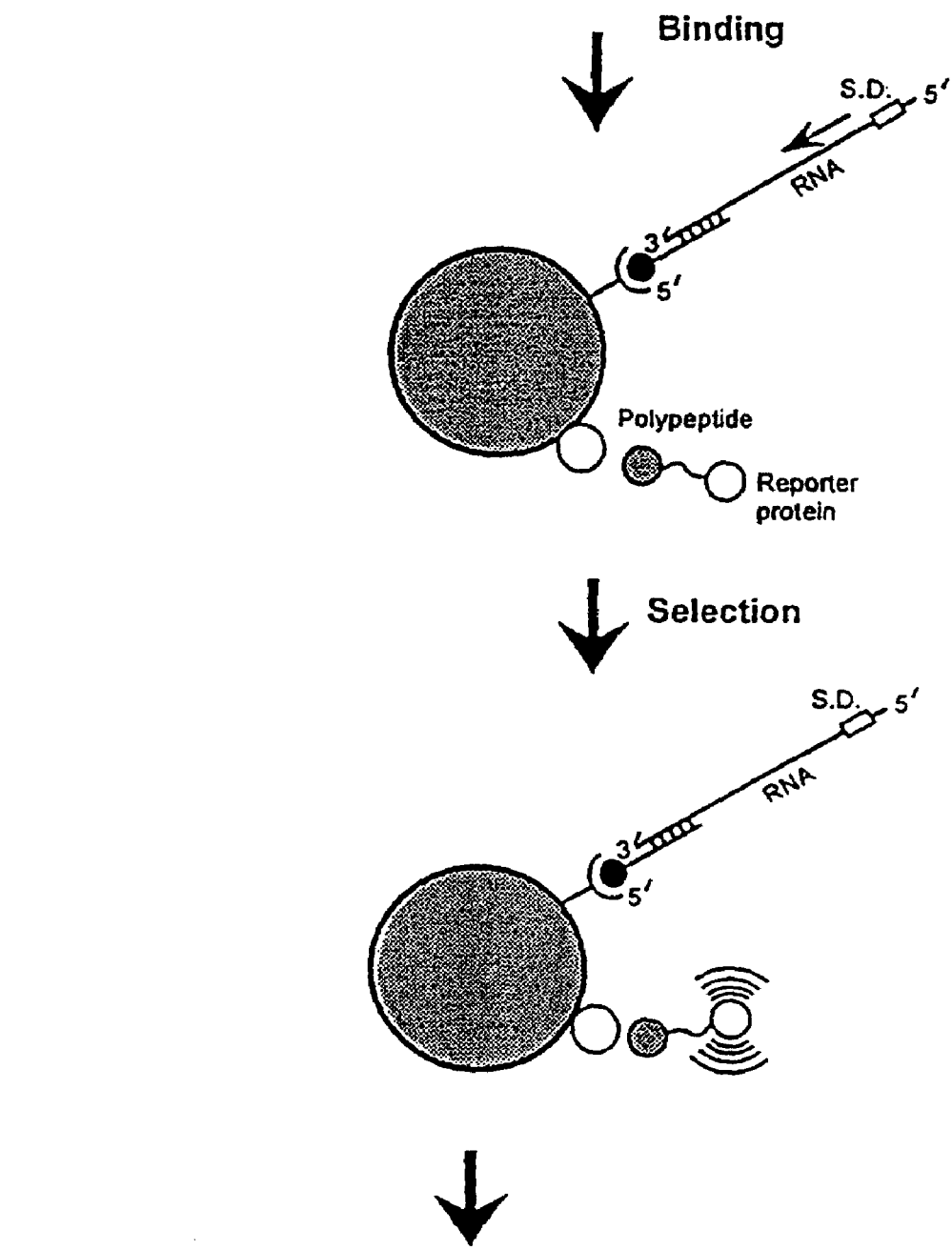

FIG. 5 is a schematic representation of the use of a solid support as carrier of coupled genetic and protein information (immobilized mRNA/labelled binder version). From a library of genetic constructs containing signals necessary for library member transcription and protein translation, RNA (mRNA) is produced (transcription) in vitro and immobilized onto particles of a suitable carrier support (e.g. via hybridization between complementary sequences present in the mRNA and immobilized DNA, PNA or RNA fragments). The particles also carry the target molecule with which library members are desired to interact. This immobilization may be obtained using e.g. standard coupling chemistries such as EDC/NHS chemistry or biotin/streptavidin chemistry. The genetic constructs (mRNA) encode individual library members as genetically fused to a reporter fusion partner (RFP) such as an enzyme or autofluorescent protein such as green fluorescent protein (GFP). After addition of components for in vitro translation (e.g. an *Escherichia coli* S30 extract), mRNA molecules are translated to produce the different protein library members. Through interaction between the immobilized target molecule and the newly translated library member, individual library members capable of interaction with the solid support immobilized target molecule are physically linked to the solid support carrier containing the genetic information (mRNA) encoding them.

After washing, the solid support carriers are sorted, e.g. using FACS technology, to isolate individual or multiple particles carrying complexes between the immobilized labelled target and the particle-associated library member gene product. Thus, particles carrying complexes between the labelled target and the particle-associated library member gene product and its genetic information (mRNA) are isolated.

Using e.g. reverse transcriptase PCR, the bead/particle-associated mRNA molecules are converted into the corresponding DNA fragments which are PCR amplified and used for consecutive rounds of in vitro transcription, particle immobilization, in vitro translation followed by selection, e.g. by FACS.

Figure 6:
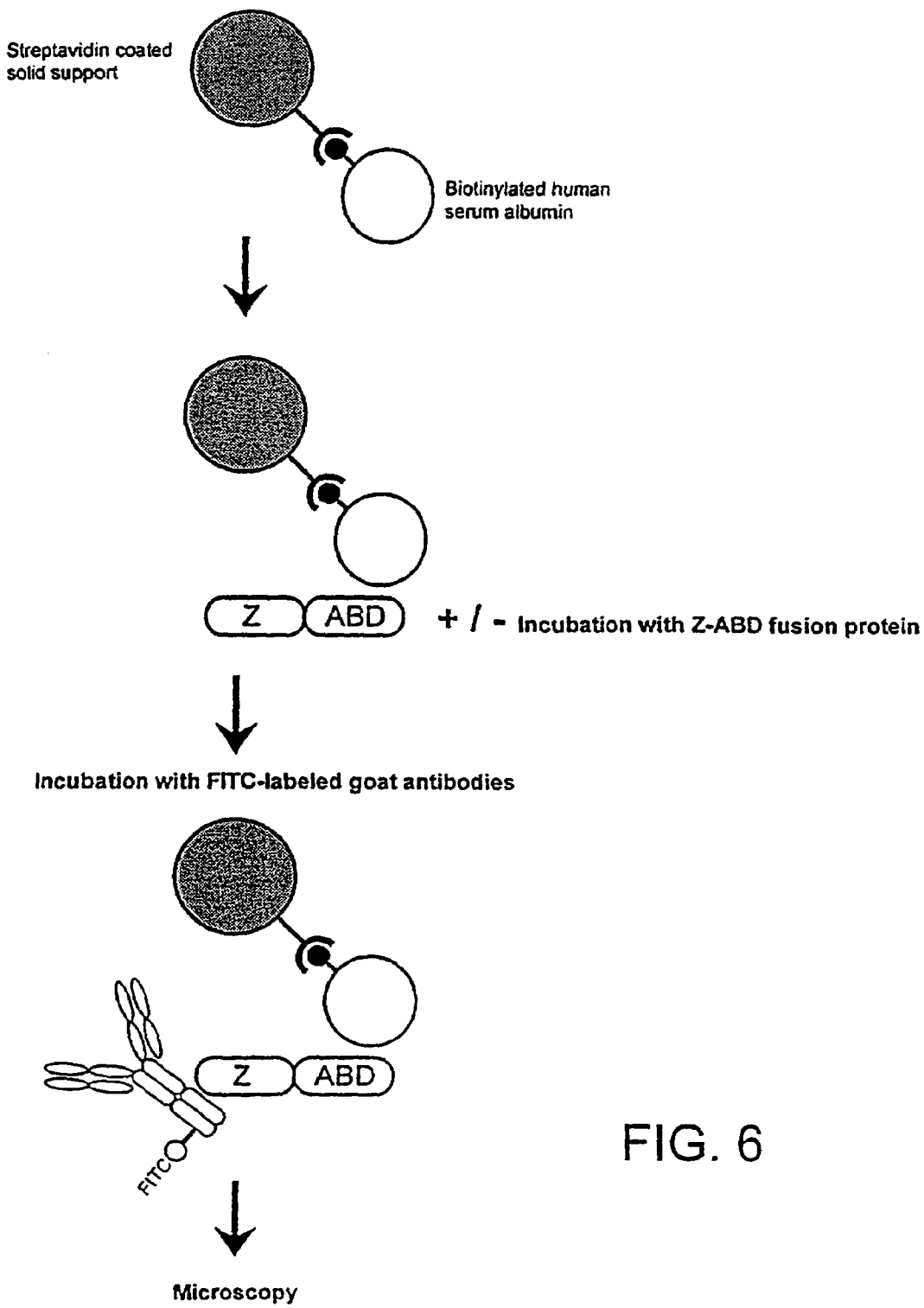

FIG. 6 illustrates the experimental set-up for Example 1. Paramagnetic particles coated with streptavidin were firstly incubated with biotinylated human serum albumin (HSA), resulting in robust anchoring of HSA. Separate aliquots were subsequently incubated with either (A) protein ABD-Z, a genetic fusion protein between a serum albumin binding protein (ABD) derived from streptococcal protein G and an immunoglobulin binding protein (Z) derived from staphylococcal protein A, followed by incubation with fluorescent isothiocyanate (FITC) conjugated polyclonal goat IgG antibodies, or (B) with the FITC conjugated goat IgG antibodies directly.

Figure 7:
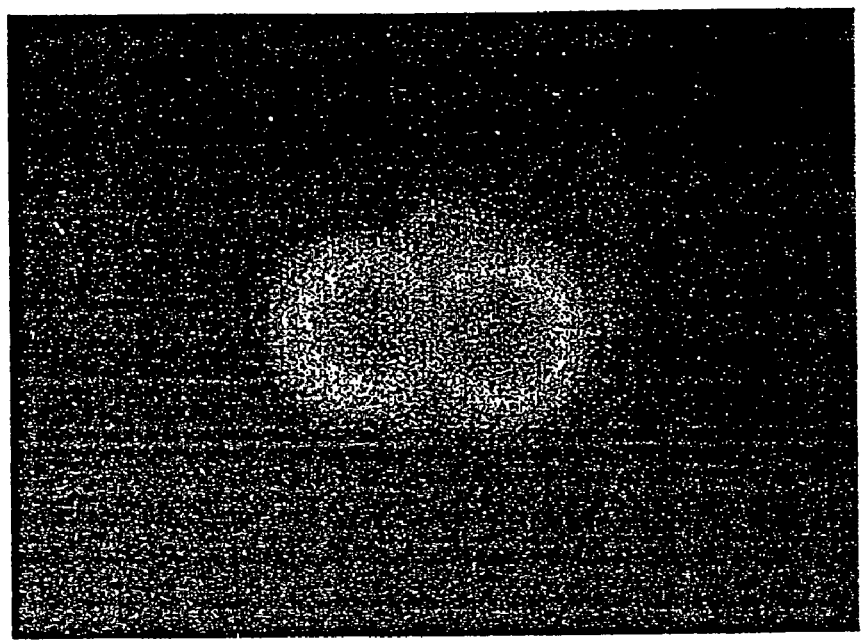
Figure 7:
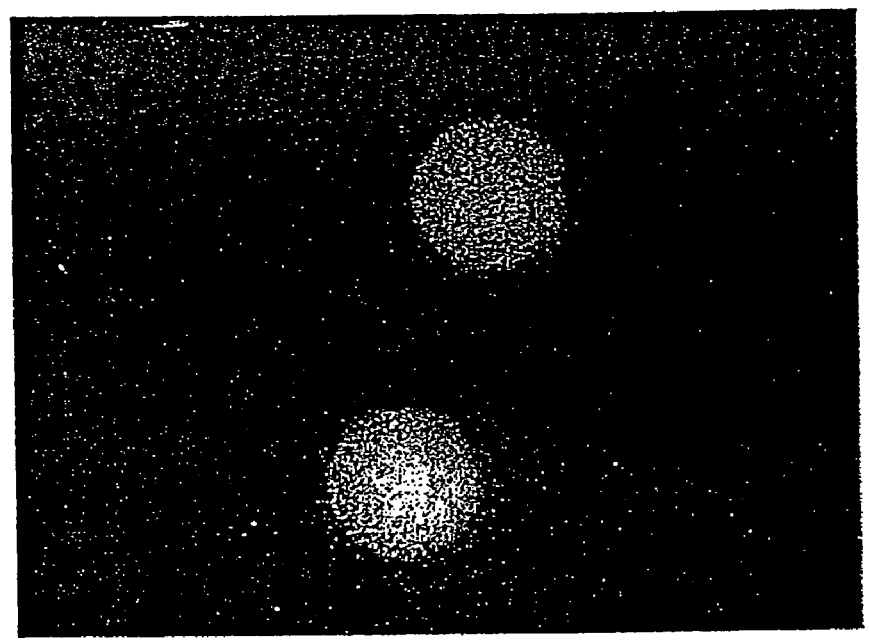

FIG. 7 is a photograph from UV-microscopy analyses of streptavidin-coated beads/particles containing streptavidin/biotin chemistry-immobilized biotinylated human serum albumin. (A) Particles incubated with FITC-conjugated polyclonal goat IgG antibodies after having first been subjected to a solution containing the fusion protein Z-ABD. (B) Particles incubated with FITC-conjugated polyclonal goat IgG antibodies only.

Figure 8:
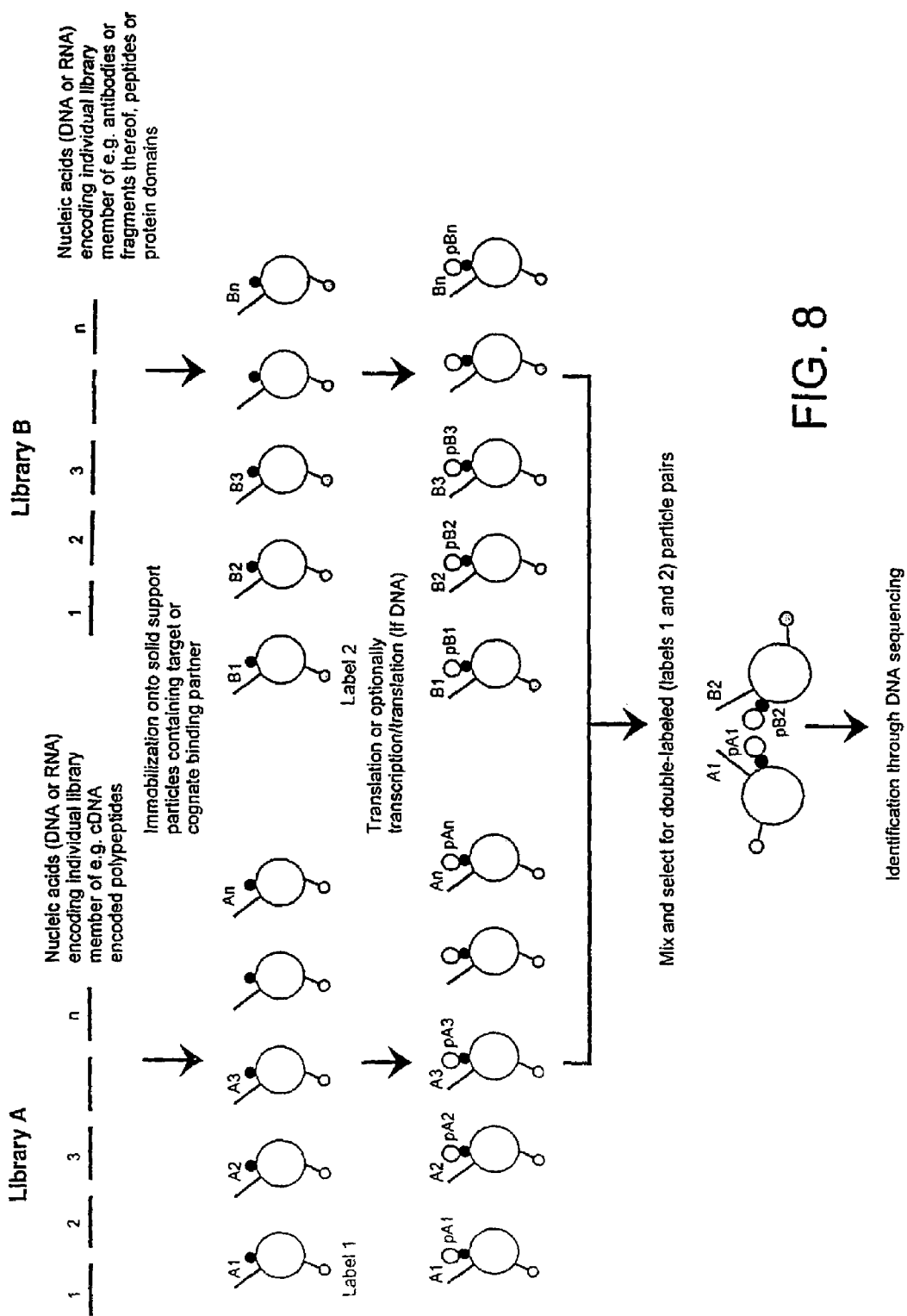

FIG. 8 is a schematic representation of the use of the invention for selecting interacting polypeptide pairs through the crossing of two different libraries. Two pools of nucleic acid fragments encoding different polypeptide libraries are separately immobilized onto particles of solid support carrier systems. In a DNA-based format, fragments are immobilized whereafter a coupled transcription/translation step is performed resulting in the production of the corresponding gene products. In an RNA-based format, RNA molecules are transcriptionally produced from the DNA fragments, after which they are immobilized onto the solid support carrier, followed by a translation step resulting in the corresponding gene products. Typically, but not exclusively, the gene products are fusion proteins between polypeptide library members and an affinity fusion partner for which a cognate binding partner is present on the particles. The different libraries are differently labelled, e.g. using two fluorophores having different excitation spectra. Biospecific interactions between members of the different polypeptide libraries are detected as double-labelled particle pairs. For identification, the nucleic acids present on the isolated particles encoding the corresponding genes are analyzed by DNA sequencing.

Figure 9:
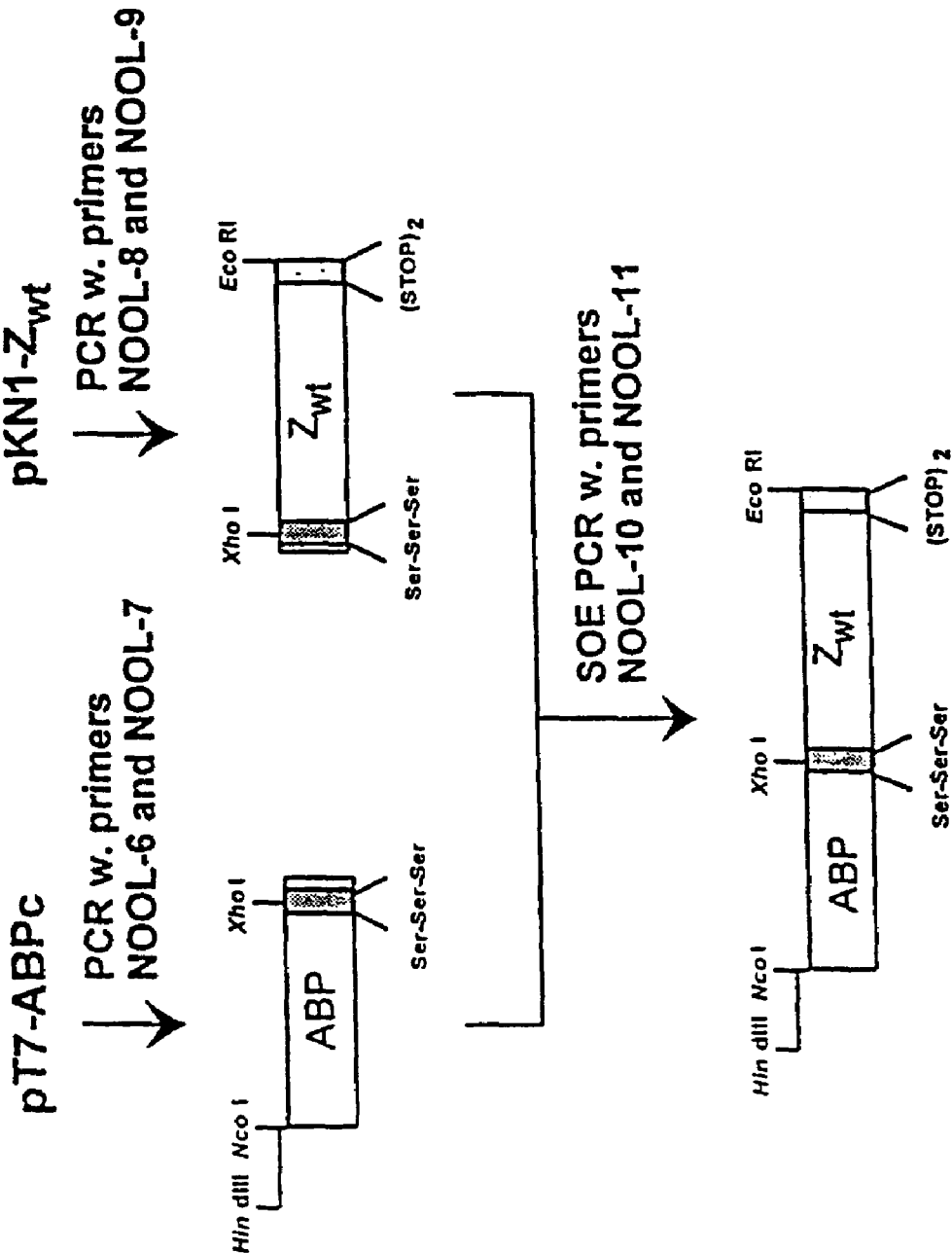
Figure 9:
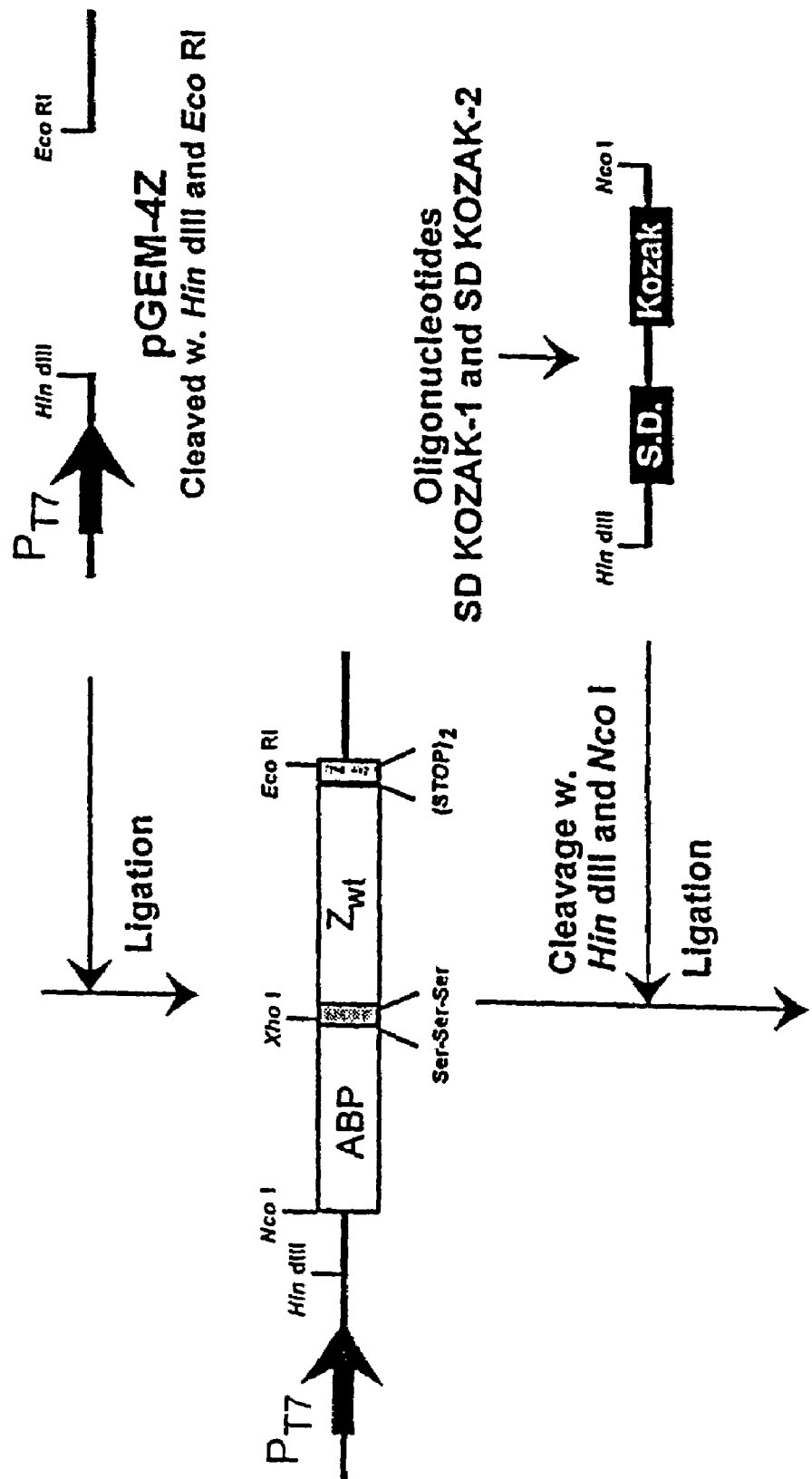
Figure 9:
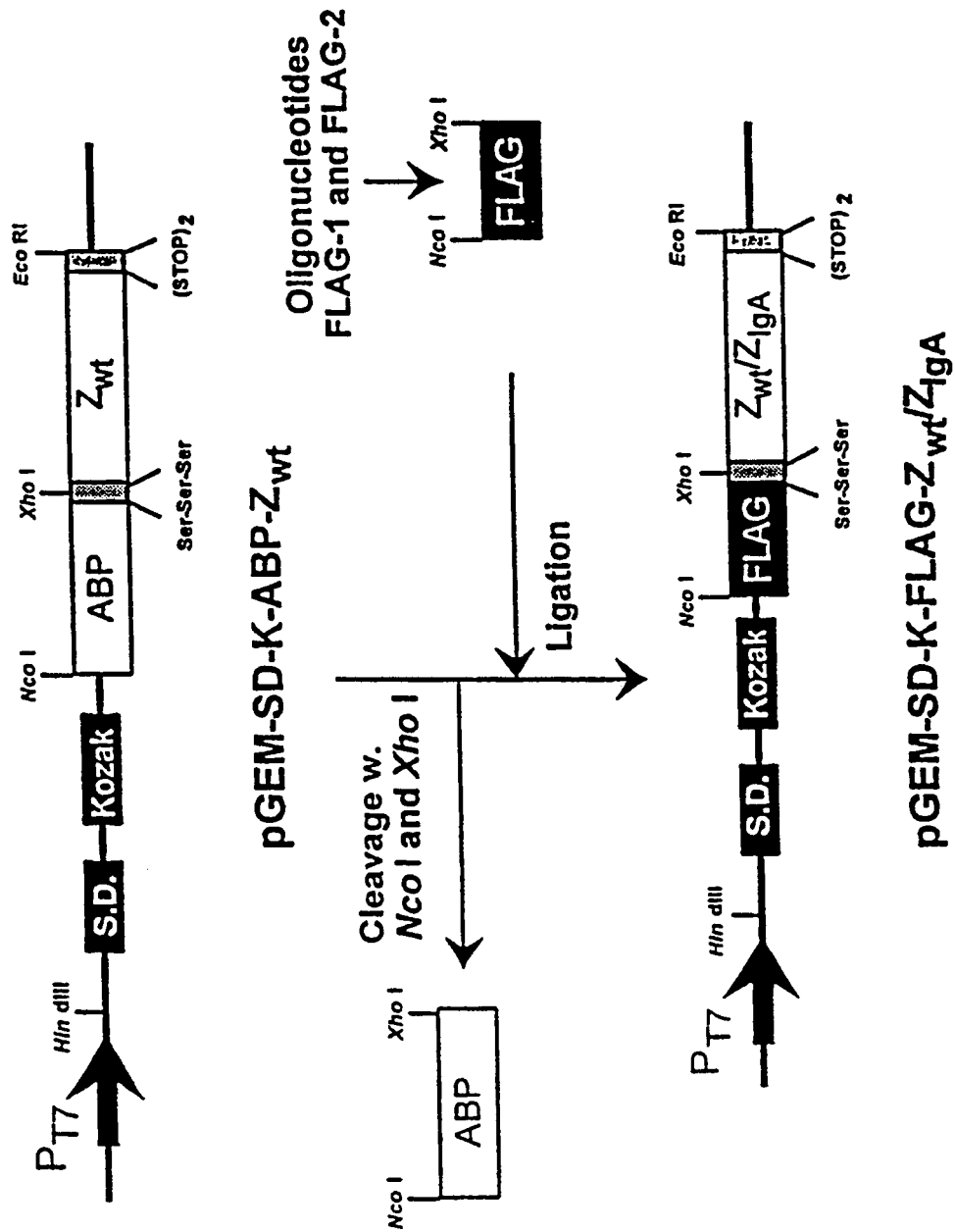

FIG. 9 is a schematic description of the construction of the plasmids pGEM-SD-K-FLAG-$Z_{wt}$ and pGEM-SD-K-FLAG-$Z_{IgA}$, designed for use as template for the amplification of PCR products for cell free transcription and translation of either free or bead-immobilized DNA/RNA.

Figure 10:
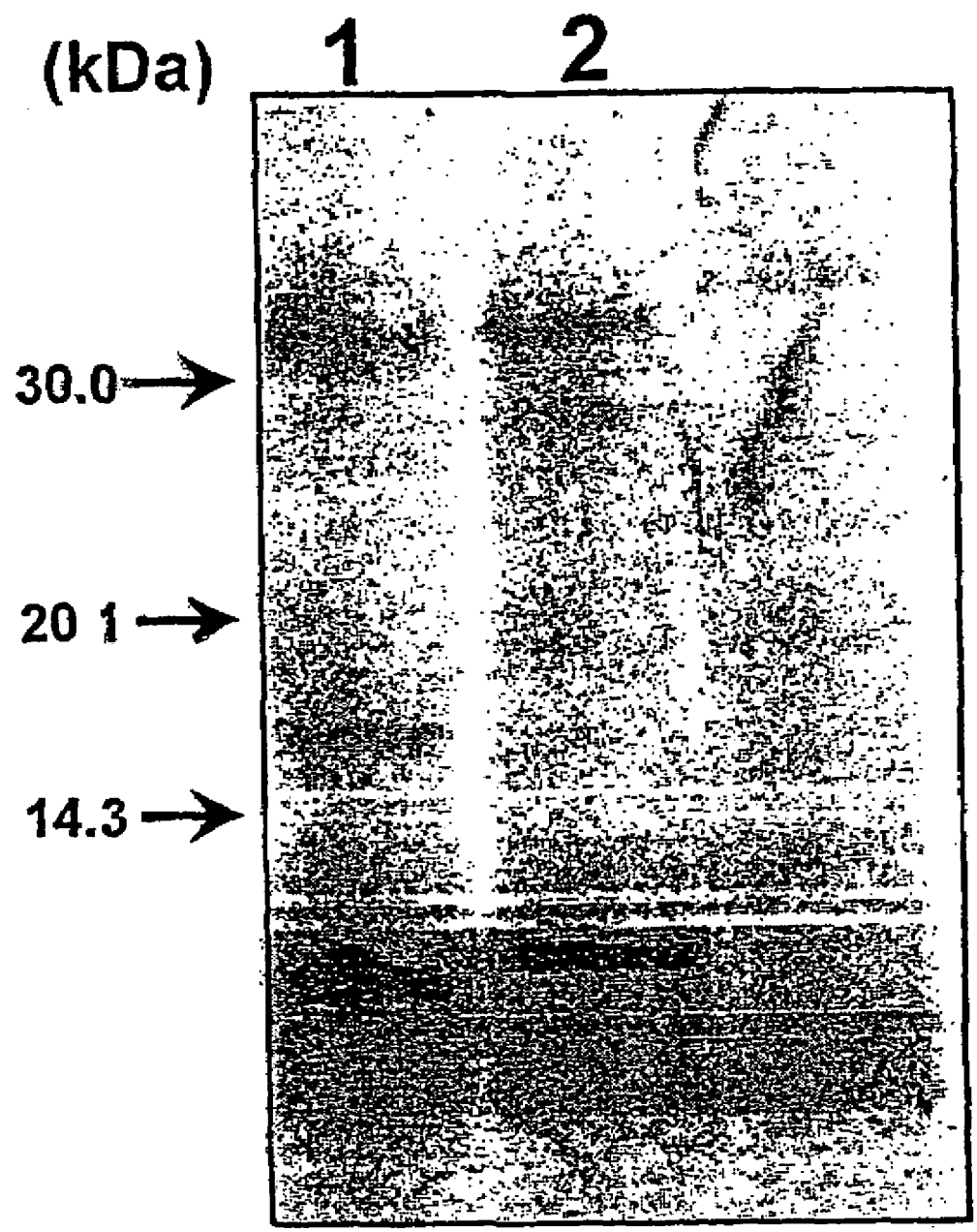

FIG. 10 is a radiograph obtained after SDS-PAGE analysis under reducing conditions of proteins synthesized using a cell free extract supplemented with [35S]methionine and PCR products produced with primers NOOL-12 and NOOL-13 using different plasmids as templates. Lane 1: pGEM-SD-K-FLAG-$Z_{wt}$, lane 2: pGEM-SD-K-FLAG-$Z_{IgA}$. A marker with 14C-labeled proteins was used as size reference (prod. no. CFA756, Amersham Pharmacia Biotech, Uppsala, Sweden). Arrows indicate the positions of reference proteins with molecular weights of 14.3, 20.1 and 30.0 kDa, respectively.

Figure 11:
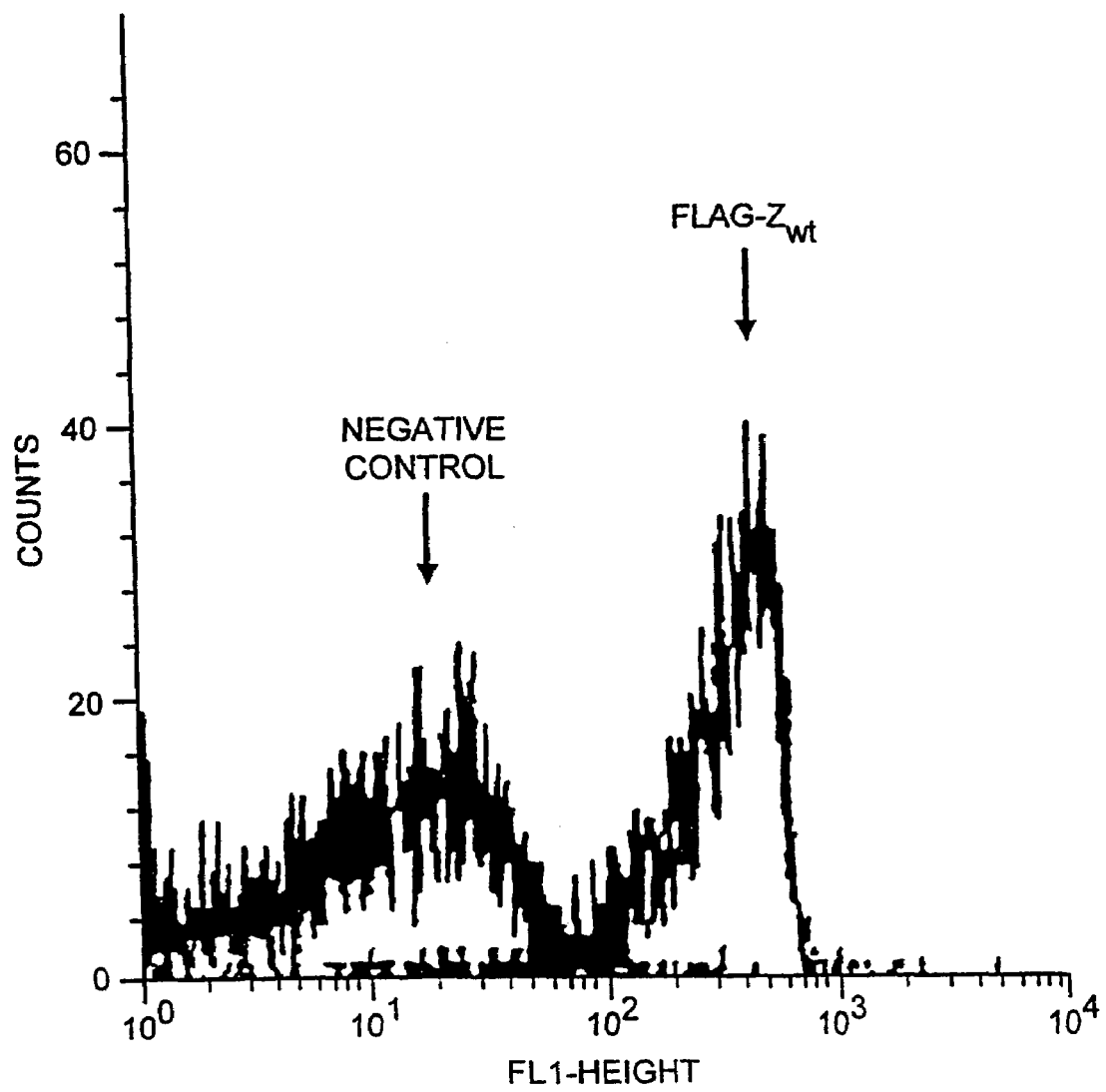

FIG. 11 is an overlay plot from a comparative FACS analysis of anti-FLAG BioM5 antibody-coated beads subjected to a FLAG-$Z_{wt}$ PCR product transcription/translation mixture and negative control beads treated in the same way but not coated with anti-FLAG BioM5 antibodies.

Figure 12:
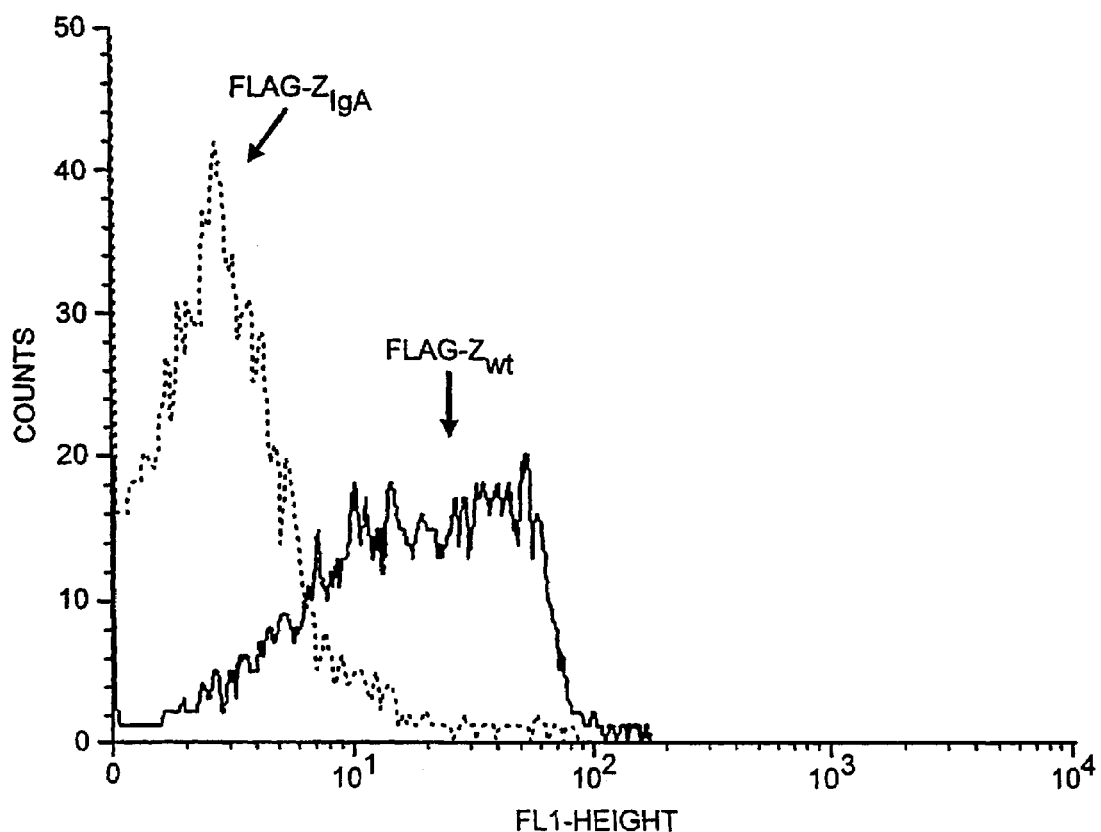

FIG. 12 is an overlay plot from a comparative FACS analysis of anti-FLAG BioM5 antibody and PCR product doubly coated beads, subjected to a transcription/translation mixture, followed by detection. The picture shows the analysis of two different sets of beads containing either FLAG-$Z_{wt}$ or FLAG-$Z_{IgA}$ encoding PCR products subjected to the analysis.

FIG. 13(A) is a schematic representation of the presence of a Mlu I restriction site in the PCR product obtained by PCR amplification using primers NOOL-12 and NOOL-13 on a pGEM-SD-K-FLAG-$Z_{wt}$ plasmid template. In contrast, no Mlu I site is present in the PCR product obtained by PCR amplification using primers NOOL-12 and NOOL-13 on a pGEM-SD-K-FLAG-$Z_{IgA}$ plasmid template. Also shown are the sizes of the cleavage products obtained after incubation of the FLAG-$Z_{wt}$ fusion protein encoding PCR product after incubation with Mlu I.

(B) are photographs showing agarose gel electrophoresis analyses of PCR products obtained by PCR amplification of different samples taken before or after FACS-based enrichments. Lane 1: Beads containing FLAG-$Z_{wt}$ encoding PCR product only; lane 2: Beads containing FLAG-$Z_{wt}$ encoding PCR product only. Resulting PCR product subjected to incubation with Mlu I; lane 3: Beads containing FLAG-$Z_{IgA}$ encoding PCR product only; lane 4: Beads containing FLAG-$Z_{IgA}$ encoding PCR product only. Resulting PCR product subjected to incubation with Mlu I; lane 5: Beads containing a 1:1 mixture of FLAG-$Z_{wt}$ and FLAG-$Z_{IgA}$ encoding PCR products. Sample from before FACS enrichment experiment; lane 6: Beads containing a 1:1 mixture of FLAG-$Z_{wt}$ and FLAG-$Z_{IgA}$ encoding PCR products. Resulting PCR product subjected to incubation with Mlu I. Sample from before FACS enrichment experiment; lane 7: Sample from beads sorted in FACS enrichment experiment; lane 8: Sample from beads sorted in FACS enrichment experiment. Resulting PCR product subjected to incubation with Mlu I.

Flanking lanes with size markers (phage 1 DNA cleaved with Pst I, Amersham Pharmacia Biotech, Uppsala, Sweden) are labeled M.

Figure 13:
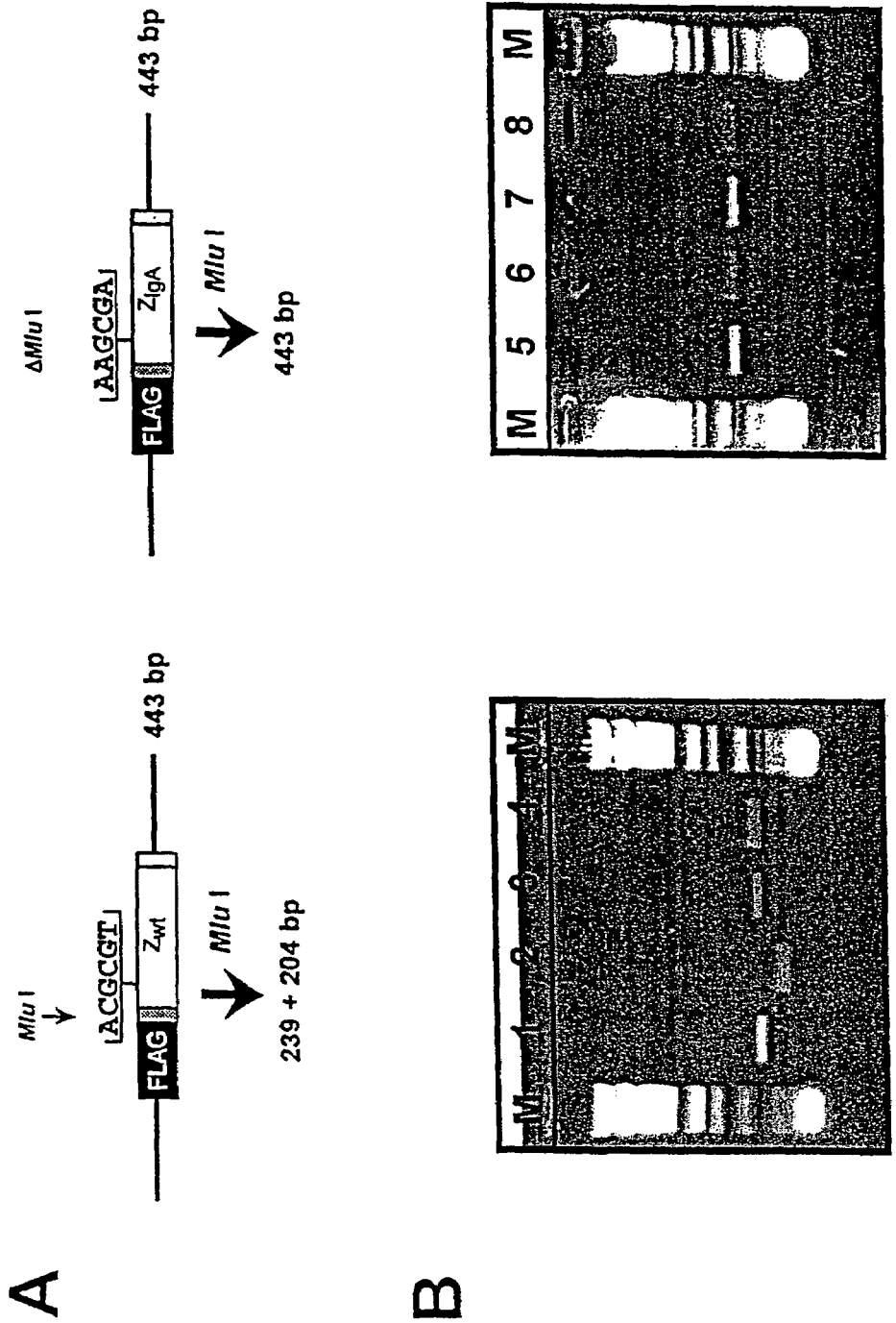
Figure 14:
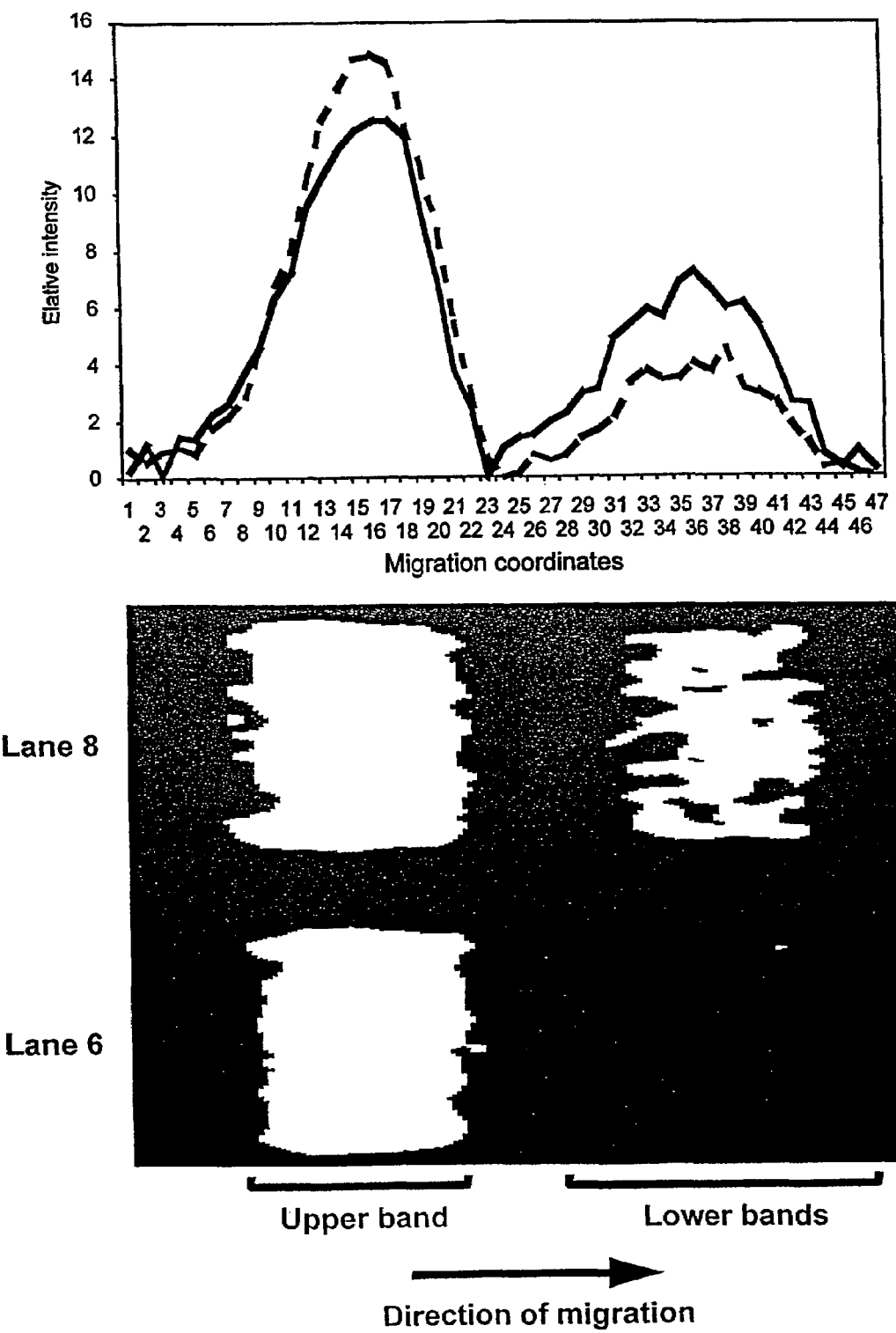

FIG. 14 Top: is an overlay plot of intensity recordings of tracks corresponding to lanes 6 (dashed line) and 8 (solid line) in FIG. 13. The relative intensity is shown as a function of the migration coordinate. Bottom: shows digitally excised tracks from the gel image corresponding to lane 6 and 8 from the gel shown in FIG. 13. A relative shift of intensity towards the smaller molecular weight cleavage products is observed for the sample obtained by PCR amplification of nucleic acids present on beads collected in the FACS enrichment (track corresponding to lane 8).

DESCRIPTION OF THE PREFERRED EMBODIMENTS

In a representative embodiment of the method of the invention a pool of gene fragments (FIGS. 2–5) containing the DNA encoding different polypeptide library members is prepared using standard DNA technology, for example as described by Nord et al., *Prot. Engineering* 8, pp. 601–608 [1995] and Nord et al., *Nature Biotechnol.* 15, pp. 772–777 [1997]. The gene fragments should include a first sequence corresponding to a suitable RNA polymerase promoter sequence, such as *E. coli* phage T7 promoter, T3 promoter, SP6 promoter, lac promoter, lac UV5 promoter, ara B promoter, trp promoter, staphylococcal protein A promoter, or viral promoters such as Raus Sarcoma Virus (RSV) promoter, and Cytomegalo virus (CMV) late and early promoters to function as signals for transcription of the DNA fragment into mRNA using a suitable extract such as an S30 extract of *E. coli* for promoters of *E. coli* or prokaryotic origin or a reticulocyte extract or wheat germ extract for promoters of eukaryotic origin (coupled systems) or by a first transcriptional step using a preparation of purified suitable RNA polymerase, separated from a later translational step (uncoupled system) in which the mRNA templates are used for translation of the genetic information into the corresponding polypeptides.

In one aspect of the invention, the promoter sequence is followed by a sequence encoding an affinity fusion partner (AFP), employed for binding a cognate binding partner immobilized onto a solid phase carrier particle. This affinity fusion partner may for example be the albumin binding region of streptococcal protein G or derivatives thereof, the immunoglobulin binding protein A or derivatives thereof, maltose binding protein, glutathione S-transferase, FLAG peptide, Bio-tag (biotinylated peptide), hexahistidyl sequence, c-myc tag, or any other polypeptide for which a suitable cognate binding partner is available. The gene fragments should each also contain the gene encoding an individual library member polypeptide, in translational frame with the affinity fusion partner polypeptide if used. Alternatively, the gene encoding the affinity fusion partner may be positioned after the gene for the polypeptide library member.

In one aspect of the invention, the sequence encoding the individual library member polypeptide is either preceded or followed by a sequence encoding a suitable reporter polypeptide, such as green fluorescent protein (GFP), alkaline phosphatase, luciferase, horse radish peroxidase (HRP) or β-galactosidase.

Figure 2:
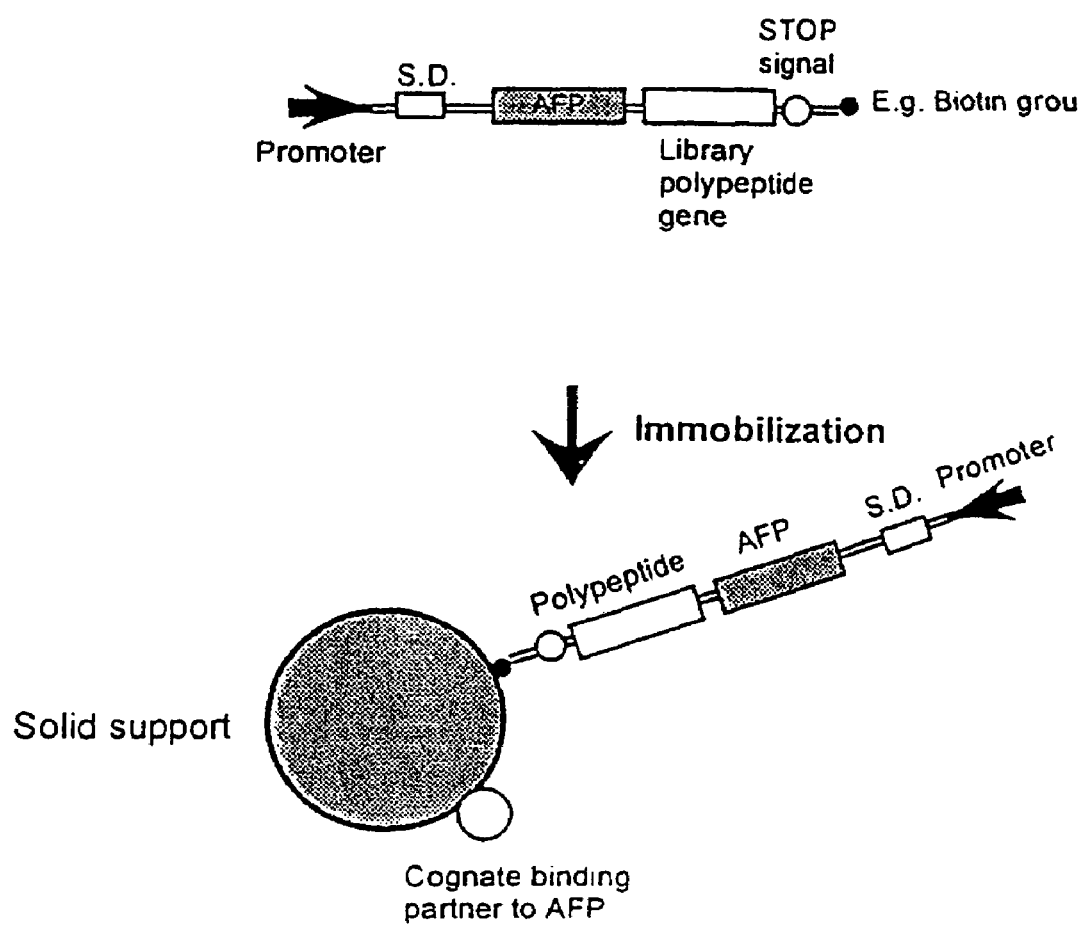
FIG. 2 is a schematic description of the use of a solid support as carrier of coupled genetic and protein information (immobilized DNA/labelled target in solution version). A library of DNA constructs (typically but not exclusively PCR fragments) containing signals necessary for library member RNA transcription and protein translation is immobilized onto particles of a suitable carrier support (e.g. using biotin/streptavidin chemistry by incorporation of a biotin group into the DNA of the primer used for the PCR amplification and the use of streptavidin coated beads). The genetic constructs encode individual library members as genetically fused to a common affinity fusion partner (AFP) for which the cognate binding partner (CBP) is immobilized onto the particles (e.g. via suitable coupling chemistry such as streptavidin/biotin chemistry). After addition of components for in vitro transcription and translation (e.g. an *Escherichia coli* S30 extract), RNA (mRNA) molecules are produced which encode for the different subsequently translated protein library members. Through interaction between the immobilized binding partner and the newly translated affinity fusion partner, the individual library members are physically linked to the solid support carrier particles containing the genetic information (DNA) encoding them.

In one aspect of the invention, the gene fragments contain a suitable chemical group (e.g. biotin or digoxin) introduced e.g. by PCR amplification using a primer or nucleotides labelled with the group. This group is used for anchoring the DNA fragment onto solid support particles coated with a suitable cognate binding partner, such as streptavidin or anti-digoxin antibody(ies) (FIGS. 2 and 4).

In another aspect of the invention, a pool of transcribed mRNA is immobilized onto the solid support particles via a suitable attachment moiety. This moiety may for example be a nucleotide sequence at the 5'- or 3'-end of the mRNA, for which a complementary sequence of RNA, DNA or PNA is immobilized onto the solid support particles (FIGS. 3 and 5).

After immobilization of DNA fragments onto the solid support particles, a transcription step is performed using a suitable RNA polymerase depending on the promoter used for the construction of the fragments. The thereby transcribed mRNA is employed for translation of the genetic information into the corresponding polypeptides which are bound to the solid support particles by biospecific interaction with either an immobilized cognate binding partner for an affinity fusion partner encoded in translational frame with the polypeptide or via recognition of a target molecule immobilized onto the particle. For the translation a suitable extract or pure components may be used such as an *E. coli* S30 extract, a rabbit reticulocyte extract or a reconstituted mixture of purified essential components of a translation machinery. Suitable particles may for example be made of polystyrene or any other polymer or mixtures of polymers, cellulose, hydroxyapatite, sepharose, dextran or silica.

After immobilization of mRNA molecules onto solid support particles, the translation of these into the corresponding proteins is performed as described above. The thereby produced polypeptides are bound to the solid support particles by biospecific interaction with either an immobilized cognate binding partner for an affinity fusion partner encoded in translational frame with the polypeptide or via recognition of a target molecule immobilized onto the particle.

To circumvent cross-over reactions, i.e. the binding of a translated polypeptide fusion protein molecule to a cognate binding partner or target molecule present on a solid support particle not also carrying the genetic information (DNA or RNA) encoding the polypeptide, the mixture may be diluted so as to prevent close proximity between particles.

Figure 1:
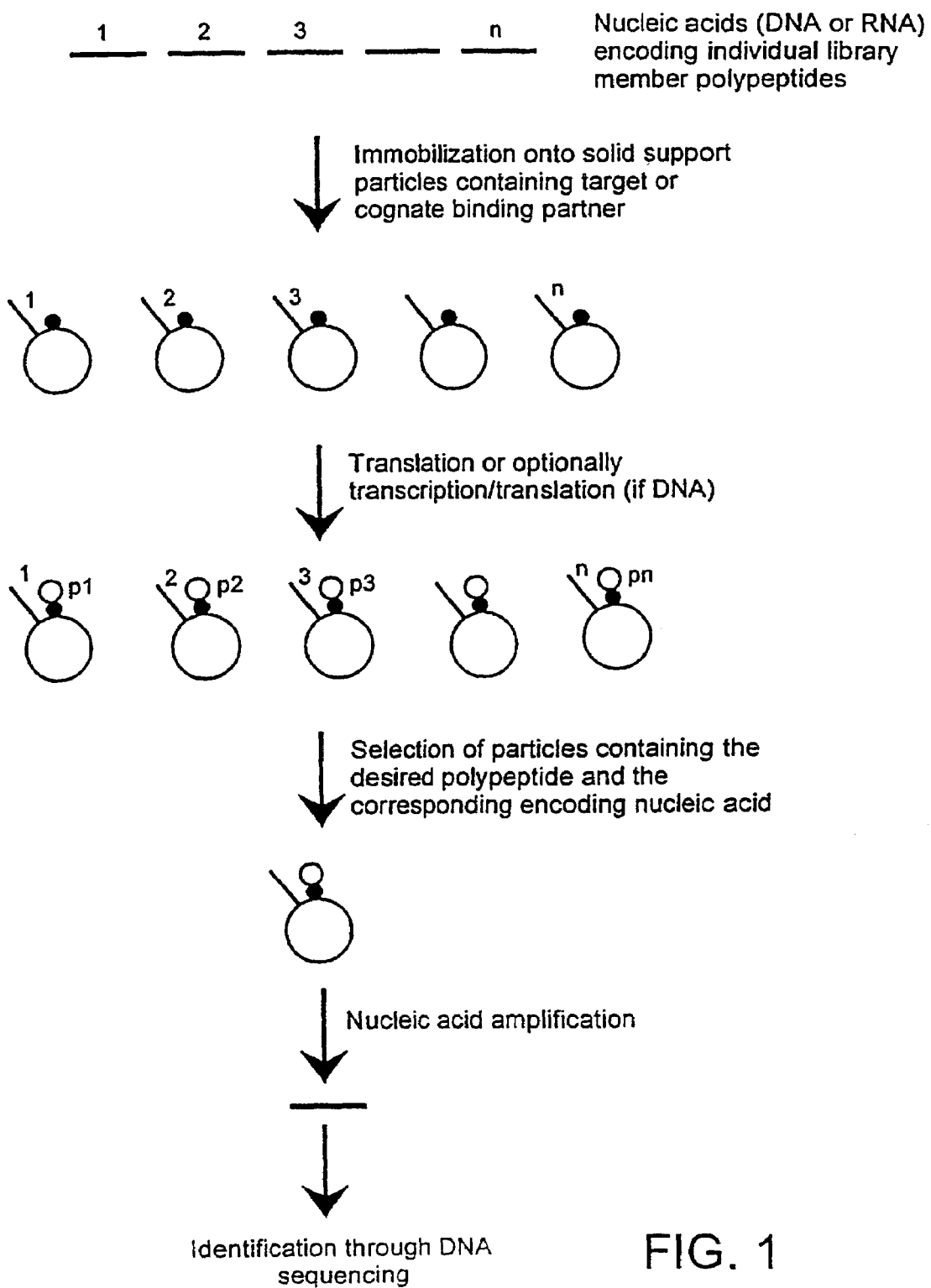
FIG. 1 is a schematic description of the basic concept of the invention. A pool of nucleic acid fragments encoding individual polypeptide library members are immobilized onto particles of a solid support carrier. In a DNA-based format, fragments are immobilized whereafter a coupled transcription/translation step is performed resulting in the production of the corresponding gene products. In an RNA-based format, RNA molecules are transcriptionally produced from the DNA fragments, after which they are immobilized onto the solid support carrier, followed by a translation step resulting in the corresponding gene products. Typically, but not exclusively, the gene products are fusion proteins between polypeptide library members and an affinity fusion partner for which a cognate binding partner is present on the solid support carrier particles. Functional selection of a desired polypeptide results in isolation of particles carrying the corresponding genes (DNA or RNA) which are identified after nucleic amplification and DNA sequencing.

Selection of particles containing a desired polypeptide or group of polypeptides may be performed by direct isolation, for example in an FACS scanner if the target is labelled with a fluorophore or if the polypeptide is genetically fused to a fluorescent protein such as green fluorescent protein. A different selection method is to use magnetic principles, using magnetic (or paramagnetic) particles coated with the target molecule of interest (FIGS. 1 and 2). Alternatively, particles labelled via a specific interaction between a library member polypeptide gene product may be physically isolated using e.g. a UV-microscope.

Selection may be performed on the basis of functional properties of the encoded polypeptides, such as binding to a desired target (antibodies or other proteins or peptides, carbohydrates, organic molecules, cells, viruses, plants etc.), catalytic activity, or through proteolytic or chemical stability under certain chemical conditions.

After isolation of particles carrying a polypeptide with the desired characteristics, the nucleic acid information (DNA or RNA) present on the same particles is amplified (if necessary) by in vitro nucleic acid amplification methods such as reverse transcriptase PCR (if RNA), PCR (if DNA), or rolling circle replication.

If necessary, the procedure may be repeated for additional cycles of direct DNA immobilization or RNA immobilization after in vitro transcription of re-amplified particle-bound nucleic acids. If further variation is desired for the next round of selection, the amplification conditions or polymerase(s) may be chosen to introduce mutations into the next pool of DNA fragments.

In yet another aspect of the invention two different libraries of polypeptides are investigated for interacting pairs (FIG. 8). Particles corresponding to a library of e.g. cDNA encoded polypeptides are mixed with particles carrying members of a polypeptide library of, for example, cDNA encoded proteins, antibodies or fragments thereof, peptides or protein domains. The particles used for the immobilization of the nucleic acids are prepared such that they contain two different labels, one for each library. Isolation of interacting pairs of polypeptides resulting from biospecific interactions are isolated by e.g. FACS technology, employing detection of double-labelled particle pairs.

The method of the invention has several advantages over existing selection systems using an in vivo polypeptide biosynthesis step, since there is no need for transformation of the genetic material into a recipient cell. The only limitation with respect to library size (complexity) is the binding capacity of the solid support system. Furthermore, the present in vitro selection system uses a robust solid support as the linkage between genotype and phenotype, enabling harsh conditions to be used when selecting ligands with high affinity towards a given target molecule. As a consequence of the nucleic acids being directly immobilized on the solid support they may easily be recovered; thus, for example, if the solid support comprises magnetic beads these may be removed from the transcription/translation mixture with a magnet, thus lowering the risk of contamination with non-immobilized nucleic acids.

The following non-limitative Example serves to illustrate the invention.

Standard Procedures:

Cloning and PCR Amplifications:

Standard cloning work including plasmid preparations, restriction enzyme cleavage and ligations etc. was performed as described in (Sambrook, J., Fritsch, E. F. and Maniatis, T. Molecular cloning: a laboratory manual, 2nd edn., Cold Spring Harbor Laboratory, New York, 1989) and according to suppliers recommendations. Restriction enzymes and ligase were purchased from either MBI Fermentas, Vilnius, Lithuania or New England Biolabs, MA, USA) PCR amplifications using plasmids or bead-immobilized PCR products as templates were performed in a GeneAmp® PCR system 9700 (PE Biosystems, Foster City, Calif., USA), using standard conditions. As primers, oligonucleotides from Table 1 were used as specified in the examples. Typically, 5 pmoles of primers were used in a 30-cycle PCR amplification using a buffer consisting of 0.2 mM deoxyribonucleoside triphosphates (dNTPs), 50 mM KCl, 2 mM MgCl2, 10 mM Tris-HCl (pH 8.5), 0.1% Tween 20 and 0.1 units of AmpliTaq® DNA polymerase (PE Biosystems). A standard PCR cycle had the follwing settings: 15 s 94° C., 20 s 55° C., 1 min 72° C. Standard agarose gel electrophoresis analyses of nucleic acids were performed using ethidium bromide for staining. *E. coli* cells used for cloning and plasmid preparations were RR1DM15 (Rüther, U. Nucl. Acids Res. 10: 5765–5772, 1982).

TABLE 1

List of oligonucleotide primers.

| Name | Sequence 5'–3' |
| --- | --- |
| NOOL-6 | GGGGGGAAGCTTGGGGGGGCCATGGCTTTAGCTGAAGCTAAAGTCTTAG |
| NOOL-7 | CTTTGTTGAATTTGTTGTCTACGCTCGAGCTAGGTAATGCAGCTAAAATTTCAT |
| NOOL-8 | ATGAAATTTTAGCTGCATTACCTAGCTCGAGCGTAGACAACAAATTCAACAAAG |
| NOOL-9 | GGGGGAATTCTTATTATTTCGGCGCCTGAGCATCAT |
| NOOL-10 | GGGGGGAAGCTTGGGGG |
| NOOL-11 | GGGGGAATTCTTATTATTTCG |
| NOOL-12 | GTTGTGTGGAATTGTGAG |
| NOOL-13 | Biotin-AAGTTGGGTAACGCCAGG |
| SD KOZAK-1 | AGCTTAATAATTTTGTTTAACTTTAAGAAGGAGATATAGC |
| SD KOZAK-2 | CATGGCTATATCTCCTTCTTAAAGTTAAACAAAATTATTA |
| FLAG-1 | CATGGACTACAAAGATGACGATGATAAAAGC |
| FLAG-2 | TCGAGCTTTTATCATCGTCATCTTTGTAGTC |

Recombinant Protein Production:

E. coli cells used for expression were either RR1DM15 (Rüther, U. Nucl. Acids Res. 10: 5765–5772, 1982) or BL21DE3 (Novagen, Madison, Wis., USA). Osmotic shock procedures were performed as described earlier (Nygren et al., J. Mol. Recognit. 1:69–74, 1988). Affinity chromatography purifications of proteins on HSA and IgG-Sepharose resins were performed as described earlier (Nygren et al., J. Mol. Recognit. 1:69–74, 1988). Human polyclonal IgG was supplied by Pharmacia and Upjohn AB, Stockholm.

Protein Biotinylation:

Human serum albumin (HSA) (prod no. A-8763, Sigma) was biotinylated using EZ-Link™ Sulfo-NHS-LC-Biotin kit (prod no. 21335, Pierce Chemical Company, Rodeford, Ill., USA).

Cell Free Transcription and Translation of PCR Fragments:

PCR products as indicated were subjected to cell free transcription and translation using a commercial E. coli S30 extract system for linear DNA (prod no. L1030, Promega, Madison, Wis., USA) according to the instructions by the manufacturer. For coupled transcription/translation of free (non-immobilized) PCR products, typically, 10–70 ng of PCR product was mixed with 50 µl of cell extract and incubated for 1 h at 25° C. In other experiments, PCR products were immobilized onto streptavidin coated microbeads (M280-SA, Dynal, Norway or Bang Laboratories, prod. no. CP01N/004109, where indicated). Such beads had previously been incubated with a 1.89 mg/ml solution of biotinylated BioM5 antibody (prod no. F-2922, Sigma, Saint Louis, Mo., USA) directed to a FLAG peptide for affinity capture of FLAG peptide-tagged proteins. Typically, 10 ng of PCR product were mixed with 1 mg of BioM5-containing beads, which were subsequently washed two times before a coupled transcription/translation reaction was performed using 25 µl of E. coli extract.

Protein Gel Electrophoresis:

Sodium dodecylsulphate polyacrylamide gel electrophoresis of proteins (SDS-PAGE) under reducing conditions was performed using the Phast system (Amersham Pharmacia Biotech, Uppsala, Sweden) or in a Novex Xcell II (San Diego, Calif., USA), as described by the respective suppliers.

DNA Sequencing:

DNA sequencing was performed by cycle sequencing (Carothers et al., BioTechniques 7:494–499, 1989; Savolainen, P., et al., Mol. Biol. Evol. 17:474–488, 2000) using ThermoSequenase DNA polymerase (Amersham Pharmacia Biotech) and primers as indicated. Sequencing reactions were loaded onto a ABI Prism 377XL instrument (PE Biosystems, Foster City, Calif., USA).

Fluorescence-Activated Cell Sorting (FACS) Experiments:

FACS analyses were performed with either a FACSCalibur, FACScan or a FACSVantage SE instrument (Becton Dickinson, Oxnard, USA).

Where indicated, horseradish peroxidase-conjugated antibodies were used for signal amplifications, using a fluorescein tyramide reagent (Boehringer Mannheim, Germany) as described by Anton and coworkers (Anton et al., J. Histochem. Cytochem. 46:771–777, 1998).

EXAMPLE 1

Discrimination between Solid Support Particles Labelled with Fluorescent Proteins through a Biospecific Interaction and Control Solid Support Particles Approximately 2 mg of streptavidin coated particles (M280-SA, Dynal, Norway) were incubated with 30 µl of a 2 mg/ml solution in PBS buffer (0.15 M NaCl, 20 mM phosphate, pH 7.2) of human serum albumin (HSA) (Sigma art. No. A-8763) biotinylated using a protein biotinylation kit (Pierce art. No. 21335) according to the manufacturers instructions. Particles were then either directly incubated with polyclonal goat IgG antibodies, labelled with FITC (Sigma art. No. F-9887) or first incubated with 30 µl of a 2 mg/ml solution in PBS of a fusion protein (Z-ABD) between a serum albumin binding protein (ABD) derived from streptococcal protein G and a immunoglobulin binding protein (Z) derived from staphylococcal protein A produced and HSA-affinity purified as previously described (Nord et al., op. cit. [1995], and [1997]). Between each incubation multiple (5–10) washings with PBS were performed to remove non-specifically bound proteins.

To investigate whether discrimination was possible between particles labelled by the FITC-labelled goat polyclonal antibodies via a biospecific interaction to the Z moiety of the Z-ABD fusion protein and particles not incubated with the Z-ABD fusion protein and thus incapable of binding the goat antibody, particles were analysed by UV-microscopy using a Olympus BH2-RFCA microscopy at an excitation wavelength of 495 nm. The results shown in FIG. 5 show that a clear difference in fluorescent intensity can be seen between the two differently treated pools of particles (FIGS. 5A and 5B). This shows that the result of a biospecific interaction between an (ABD-HSA)-immobilized fusion protein and a labelled target protein added in solution can be observed.

EXAMPLE 2

Assembly and Cloning of Genetic Constructs for Cell Free Transcription and Translation Experiments To be able to obtain PCR products encoding relevant proteins or protein library members and suitable or cell free transcription and translation experiments using solid supports as carriers for both nucleic acids and their corresponding encoded proteins, a genetic construct was assembled in the plasmid vector pGEM-4Z (FIG. 9). In a splice overlap extension (SOE) PCR reaction using primers NOOL-10 and NOOL-11 (table 1), two gene fragments encoding an albumin binding protein (APB) (Larsson, et al., Prot. Expr. Purif. 7:447–457, 1996) and the Z domain ($Z_{wt}$) (Nilsson et al., Prot. Engineering 1:107–113, 1987), respectively, were joined. The two fragments had previously been produced by separate PCR reactions using pT7-ABPc (ABP) (Larsson, et al., Prot. Expr. Purif. 7:447–457, 1996) (primers NOOL-6 and NOOL-7, table 1) or pKN1-$Z_{wt}$ (Nord et al., Prot. Engineering, 8:601–608, 1995) (primers NOOL-8 and NOOL-9, table 1) as plasmid templates, respectively. In the SOE reaction, two fragments were joined resulting in an ABP-(Ser)3-$Z_{wt}$ encoding gene fragment comprising in the 5'-end recognition sites for the two enzymes Hin dIII and Nco I, and in the 3'-end two translational stop codons and a recognition site for the restriction enzyme Eco RI (FIG. 9). This fragment was inserted by ligation as a Hin dIII-Eco RI fragment into the plasmid pGEM-4Z, cleaved with the same enzymes, resulting in the construct pGEM-ABP-$Z_{wt}$.

A fragment was assembled by the annealing of the two oligonucleotides SD KOZAK-1 and SD KOZAK-2 (table 1), resulting in a 40 bp fragment comprising an *E. coli* Shine Dalgarno (SD) sequence (for efficient *E. coli* translation) and a Kozak sequence (to facilitate expression in cell extracts from mammalian sources), flanked by Hin dIII and Nco I restriction sites (FIG. 9). This fragment was inserted by ligation into pGEM-ABP-Z cleaved with Hin dIII and Nco I, resulting in the plasmid vector pGEM-SD-K-ABP-$Z_{wt}$. This vector was subsequently cleaved with enzymes Nco I and Xho I, releasing the ABP encoding fragment. The thereby obtained vector fragment was ligated to a FLAG peptide encoding gene fragment, previously obtained by annealing the two oligonucleotides FLAG-1 and FLAG-2 (table 1), resulting in the vector pGEM-SD-K-FLAG-Z. This vector thus encodes a FLAG-$Z_{wt}$ fusion protein, linked by a (Ser)3 linker (FIG. 9). The vector also contains an upstream T7 promoter which is capable of driving the transcription of the FLAG-$Z_{wt}$ fusion protein gene by the action of T7 RNA polymerase. From this vector, any suitable gene fragment inserted between the Xho I and Eco RI sites can be transcribed as an mRNA operatively linked to a SD sequence, a Kozak sequence and a FLAG peptide encoding part. In addition, using primers NOOL-12 and NOOL-13 (table 1), PCR products can be obtained which are suitable for T7 RNA polymerase driven transcription and are biotinylated in their 3'-ends, suitable for immobilization on e.g. streptavidin coated surfaces and other solid supports.

To construct the vector denoted pGEM-SD-K-FLAG-$Z_{IgA}$, in which the $Z_{wt}$ encoding gene fragment has been substituted for a gene fragment encoding the human IgA-binding protein $Z_{IgA}$ (Gunneriusson et al., J. Bact. 1999), a $Z_{IgA}$ encoding gene fragment was amplified using primers NOOL-8 and NOOL-9 using a plasmid pKN1-$Z_{IgA}$ template (Gunneriusson et al., J. Bact. 1999). The resulting PCR product was cleaved with restriction enzymes Xho I and Eco RI and inserted into the vector pGEM-SD-K-FLAG-$Z_{wt}$, previously cleaved with the same enzymes. The resulting vector pGEM-SD-K-FLAG-$Z_{IgA}$ thus encodes a FLAG-$Z_{IgA}$ fusion protein, linked by a (Ser)3 linker (FIG. 9).

EXAMPLE 3

Cell Free Transcription/Translation of FLAG-$Z_{wt}$ and FLAG-$Z_{IgA}$ Fusion Proteins from their Respective PCR Products.

Using the plasmid vectors pGEM-SD-K-FLAG-$Z_{wt}$ and pGEM-SD-K-FLAG-$Z_{IgA}$, respectively, for PCR amplifications using the primers NOOL-12 and NOOL-13 (table 1), PCR products were obtained of which approx. 70 ng were subjected to a one hour cell free transcription/translation at 25° C. using 50 µl of an *E. coli* S30 cell extract (L1030, Promega, MA, USA), supplemented with [$^{35}$S]methionine and 1600 units of T7 RNA polymerase. Samples of the different transcription/translation mixtures were analyzed by 10% NuPAGE (Novex, San Diego, Calif., USA) under reducing conditions through the addition of 50 mM DTT (final concentration) in the sample loading buffer (NuPAGE LDS sample buffer, Novex) followed by exposure of the gel to a film (Kodak XOMAT-AR, 18×24 cm) at −70° C. over night. The development of the film revealed radioactive protein of expected sizes (~8 kDa) for both the FLAG-$Z_{wt}$ and the FLAG-$Z_{IgA}$ encoding PCR products (FIG. 10). This shows that the constructed plasmid vectors pGEM-SD-K-FLAG-$Z_{wt}$ and pGEM-SD-K-FLAG-$Z_{IgA}$, both were suitable for use as templates for the amplification of PCR products capable of directing a T7 RNA polymerase driven transcription of mRNA which could be used for cell free translation of FLAG-$Z_{wt}$ and FLAG-$Z_{IgA}$ fusion proteins in an *E. coli* S30 extract.

EXAMPLE 4

Immobilization of FLAG-$Z_{wt}$ and FLAG-$Z_{IgA}$ Fusion Proteins on Anti-FLAG Antibody-Containing Beads To investigate the functionality of the FLAG peptide moieties of the fusion proteins FLAG-$Z_{wt}$ and FLAG-$Z_{IgA}$ reaction mixtures obtained from production of the two fusion proteins from their respective PCR products using cell free transcription/translation as described in example 3 were mixed for three hours at room temperature with streptavidin coated M-280-SA dynabeads (Dynal, Norway) (50 mg) previously incubated with 5 µl of a 1.89 mg/ml solution of biotinylated anti-FLAG BioM5 monoclonal antibodies (Sigma) in PBS (0.15 M NaCl, 20 mM phosphate, pH 7.2). In the experiment, beads which had not been incubated with the biotinylated anti-FLAG BioM5 antibody solution were also included (control). The beads were subsequently washed with PBST (PBS with 0.1% Tween 20) and analyzed using a Beckman LS6000 SC scintillator (Beckman-Coulter, Fullerton, Calif., USA), under standard conditions using scintillation buffer. The measured signals from anti-FLAG BioM5-coated beads subjected to the transcription/translation mixtures corresponding to the FLAG-$Z_{wt}$ and FLAG-$Z_{IgA}$ fusion protein, respectively, were significantly higher compared to the negative controls (Table 2). This shows that fusion proteins, here exemplified by the two fusion proteins FLAG-$Z_{wt}$ and FLAG-$Z_{IgA}$, can be produced from their respective PCR products by cell free transcription/translation containing a functional affinity fusion partner, here exemplified by the FLAG peptide, which is suitable for immobilization of the proteins to beads containing a cognate affinity partner, here exemplified by the BioM5 anti-FLAG monoclonal antibody.

Table 2. Measured scintillation signals (accumulated under 1 min) from native streptavidin (SA) beads or streptavidin beads coated with biotinylated anti-FLAG BioM5 antibody, respectively, after mixing (and subsequent washing) with transcription/translation mixtures from different samples.

| Beads | Transcription/ translation mix | Signal (cpm) |
| --- | --- | --- |
| native SA beads | FLAG-$Z_{wt}$ | 4858 |
| BioM5 anti-FLAG coated | FLAG-$Z_{wt}$ | 34966 |
| native SA beads | FLAG-$Z_{IgA}$ | 5959 |
| BioM5 anti-FLAG coated | FLAG-$Z_{IgA}$ | 43727 |

EXAMPLE 5

Cell Free Transcription/Translation of a FLAG-$Z_{wt}$ Encoding PCR Product, Biospecific Immobilization of the Gene Product onto Beads and Analysis by Fluorescence-Activated Cell Sorting (FACS)

Cell free transcription and translation of a PCR product obtained by PCR amplification with primers NOOL-12 and NOOL-13 (Table 1) on a pGEM-SD-K-FLAG-$Z_{wt}$ plasmid template was performed as in example 3, but without the addition of [$^{35}$S]methionine. The resulting mixture was incubated for 2 hours with 50 mg streptavidin-coated polystyrene beads with a diameter of approximately 0.95 mm) (Bangs Laboratories, Fishers, Ind., USA), previously incubated with 5 µl of a 1.89 mg/ml solution of biotinylated anti-FLAG BioM5 monoclonal antibodies. In the experiment, beads not coated with the biotinyalted BioM5 anti-FLAG antibody were also included, as a control. After thorough washing with TNT buffer (0.1 M Tris-HCl pH 7.5, 0.15 M NaCl, 0.05% Tween 20), rabbit anti-DNP IgG antibodies conjugated to horse-radish peroxidase (HRP) (art. no. P0402, Dako, Denmark) were added to the beads and incubated for 45 min at 25° C., followed by washing with TNT buffer, to detect the translated and biospecifically immobilized FLAG-$Z_{wt}$ fusion protein gene product via the biospecific interaction between the constant parts (Fc) of the rabbit antibodies and the Z domain moiety of the fusion protein. To obtain a signal useful for FACS, the enzymatic activity of the HRP conjugated to the rabbit antibodies was used through the addition of one ml of a signal amplification mixture containing fluorescein tyramide (Anton et al. J. Histochem. Cytochem. 46:771–777, 1998). Between each incubation step the beads were thoroughly washed, centrifuged for 3 min at 2000×g followed by resuspension in TNT buffer (0.1 M Tris-HCl pH 7.5, 0.15 M NaCl, 0.05% Tween 20) to remove non-specifically bound protein. TNB blocking buffer (0.1 M Tris-HCl pH 7.5, 0.15 M NaCl, 0.5% Blocking reagent from Tyramide Signal Amplification kit, NEN Life Science, Boston, Mass., USA) was used during the incubation steps according to the manufacturers instructions.

After an incubation for five minutes at 25° C., and subsequent washing, the beads were resuspended in PBS for FACS analysis. This analysis showed that beads coated with the biotinylated BioM5 anti-FLAG antibody, incubated with the transcription/translation mixture of the FLAG-$Z_{wt}$ encoding PCR product could, subsequently incubated with the rabbit anti-DNP IgG-HRP conjugate and finally subjected to the signal amplification mixture containing fluorescein tyramide displayed significantly higher fluorescence signals in the FACS analysis than beads treated in the same way, but not containing the BioM5 anti-FLAG antibody (FIG. 11).

This shows that fusion proteins, here exemplified by the fusion protein FLAG-$Z_{wt}$, can be produced from a corresponding PCR product by cell free transcription/translation containing a functional affinity fusion partner, here exemplified by the FLAG peptide, which is capable of resulting in a biospecific immobilization of the protein to beads containing a cognate affinity partner, here exemplified by the BioM5 anti-FLAG monoclonal antibody, and that such beads can be detected by FACS analysis using a suitable combination of detection reagents, here exemplified by a rabbit anti-DNP IgG-HRP conjugate and a signal amplification mixture containing fluorescein tyramide.

EXAMPLE 6

Cell Free Transcription/Translation of a Bead-Immobilized FLAG-$Z_{wt}$ Encoding PCR Product, Biospecific Immobilization of the Gene Product onto Beads and Analysis by Fluorescence-Activated Cell Sorting (FACS)

Biotinylated PCR fragments encoding a FLAG-$Z_{wt}$ fusion protein, obtained after PCR amplification using primers NOOL-12 and NOOL-13 on a plasmid pGEM-SD-K-FLAG-$Z_{wt}$ template were immobilized on streptavidin-coated beads (Bangs Laboratories) at a concentration of approximately 10 ng/mg beads. The beads (50 mg) had previously been incubated with 5 µl of a solution containing 1.89 mg/ml of a biotinylated anti-FLAG peptide antibody (BioM5, Sigma). The beads containing both the biotinylated PCR products and the anti-FLAG peptide antibody were subjected to cell free transcription and translation using 25 ml of an S30 extract (Promega, Madison, Wis., USA), supplemented with 200 units of T7 RNA polymerase (Epicentre, Madison, Wis., USA) and 40 units of rRNasin (Promega, Madison, Wis., USA). After incubation for one hour at 25° C., followed by repeated washing using TNT buffer (0.1 M Tris-HCl pH 7.5, 0.15 M NaCl, 0.05% Tween 20), rabbit anti-DNP IgG antibodies conjugated to horse-radish peroxidase (HRP) (art. no. P0402, Dako, Denmark) were added to the beads and incubated overnight at 4° C. (end-over-end mixing), followed by washing with TNT, to detect the translated and biospecifically immobilized FLAG-$Z_{wt}$ fusion protein gene product via the biospecific interaction between the constant parts (Fc) of the rabbit antibodies and the Z domain moiety of the fusion protein (Nilsson et al., Protein engineering, 1: 107–113, 1987).

To obtain a signal useful for FACS, the enzymatic activity of the HRP conjugated to the rabbit antibodies was used through the addition of one ml of a signal amplification mixture containing fluorescein tyramide (Anton et al. J. Histochem. Cytochem. 46:771–777, 1998). Between each incubation step the beads were thoroughly washed, centrifuged for 3 min at 2000×g followed by resuspension in TNT buffer (0.1 M Tris-HCl pH 7.5, 0.15 M NaCl, 0.05% Tween 20) to remove non-specifically bound protein. TNB blocking buffer (0.1 M Tris-HCl pH 7.5, 0.15 M NaCl, 0.5% Blocking reagent from Tyramide Signal Amplification kit, NEN Life Science, USA) was used during the incubation steps according to the manufacturers instructions. As a negative control, streptavidin coated beads, containing immobilized BioM5 anti-FLAG antibodies, and a PCR products obtained from PCR amplification using primers NOOL-12 and NOOL-13 on a plasmid pGEM-SD-K-FLAG-$Z_{IgA}$ template were included in the experiment.

The results from the FACS analysis shows that the beads containing the immobilized biotinylated PCR fragments encoding a FLAG-$Z_{wt}$ fusion protein, obtained after PCR amplification using primers NOOL-12 and NOOL-13 on a plasmid pGEM-SD-K-FLAG-$Z_{wt}$ template display a significantly higher fluorescence intensity than the control beads containing immobilized PCR products encoding a fusion protein not recognized by the reagent rabbit-HRP conjugate used for detection (FIG. 12). This shows that fusion proteins, here exemplified by the fusion protein FLAG-$Z_{wt}$, can be produced from a corresponding, bead-immobilized, PCR product by cell free transcription/translation, containing a functional affinity fusion partner, here exemplified by the FLAG peptide, which is capable of resulting in a biospecific immobilization of the protein to beads containing a cognate affinity partner, here exemplified by the BioM5 anti-FLAG monoclonal antibody, and that such beads can be detected by FACS analysis using a suitable combination of detection reagents, here exemplified by a rabbit anti-DNP IgG-HRP conjugate and a signal amplification mixture containing fluorescein tyramide.

EXAMPLE 7

Fluorescence-Activated Cell Sorting (FACS)-Based Enrichment of Beads Containing Immobilized PCR Products Encoding a Desired Gene Product Biotinylated PCR fragments encoding FLAG-$Z_{wt}$ and FLAG-$Z_{IgA}$ fusion proteins, respectively, obtained after PCR amplification using primers NOOL-12 and NOOL-13 on plasmids pGEM-SD-K-FLAG-$Z_{wt}$ and pGEM-SD-K-FLAG-$Z_{IgA}$ templates, respectively were separately immobilized on streptavidin-coated beads (Bangs Laboratories) to a level of approximately 10 ng/mg beads. The beads (50 mg) had previously been incubated with 5 µl of a solution containing 1.89 mg/ml of a biotinylated anti-FLAG peptide antibody (BioM5, Sigma, Saint Louis, Mo., USA). Beads from the two pools were subsequently mixed at a ratio of 1:1 (equal amounts of beads of both sorts) and subjected to cell free transcription and translation using 25 ml of an S30 extract (Promega, Madison, Wis., USA), supplemented with 200 units of T7 RNA polymerase (Epicentre) and 40 units of rRNasin (Promega). After incubation for one hour at 25° C., followed by repeated washing using TNT buffer (0.1 M Tris-HCl pH 7.5, 0.15 M NaCl, 0.05% Tween 20), rabbit anti-DNP IgG antibodies conjugated to horse-radish peroxidase (HRP) (art. no. P0402, Dako, Denmark) were added to the beads and incubated for overnight at 4° C., followed by washing with TNT, to detect the translated and biospecifically immobilized FLAG-$Z_{wt}$ fusion protein gene product via the biospecific interaction between the constant parts (Fc) of the rabbit antibodies and the Z domain moiety of the fusion protein. To obtain a signal useful for FACS, the enzymatic activity of the HRP conjugated to the rabbit antibodies was used through the addition of one ml of a signal amplification mixture containing fluorescein tyramide (Anton et al. J. Histochem. Cytochem. 46:771–777, 1998). Between each incubation step the beads were thoroughly washed, centrifuged for 3 min at 2000×g followed by resuspension in TNT buffer (0.1 M Tris-HCl pH 7.5, 0.15 M NaCl, 0.05% Tween 20) to remove non-specifically bound protein. TNB blocking buffer (0.1 M Tris-HCl pH 7.5, 0.15 M NaCl, 0.5% Blocking reagent from Tyramide Signal Amplification kit, NEN Life Science, Boston, Mass., USA) was used during the incubation steps according to the manufacturers instructions. Using FACS, a bead pool originally obtained by the mixing at the 1:1 bead ratio was subsequently subjected to enrichment experiment based on fluorescence intensity. In this procedure the settings in the FACS instrument were adjusted for preparative isolation of single beads (singlets) having a relative fluorescence intensity above 50. With this setting, the mixture was subjected to sorting and tubes with approximately 4500 sorted beads were collected.

To analyze if beads carrying the PCR products encoding the FLAG-$Z_{wt}$ fusion protein, which should be specifically labeled by the labeling procedure involving the rabbit IgG-HRP conjugate, were enriched relative to beads carrying the PCR products and FLAG-$Z_{IgA}$ fusion proteins not being recognized by the rabbit IgG-HRP conjugate, the difference in DNA sequence between the two PCR products was employed.

The FLAG-$Z_{wt}$ fusion protein-encoding PCR products contain a recognition sequence for the enzyme Mlu I, not present in the PCR products encoding the FLAG-ZIgA fusion protein. This allowed for a discrimination between the two PCR products through an analysis of the susceptibility for Mlu I digestion (FIG. 13A). Samples of beads from before and after sorting were therefore subjected to PCR amplification using primers NOOL-12 and NOOL-13, which anneals at sites in the immobilized PCR products flanking the regions which differs between the two PCR product species, and therefore could be use for the simultaneous amplification of both PCR product species. Subsequent incubation of the resulting new PCR products with the restriction enzyme Mlu I could therefore be used to investigate the relative ratios between the two species in samples from before and after sorting, by analysis of DNA fragment sizes and band intensities after agarose gel electrophoresis followed by ethidium bromide staining.

A PCR amplification of the nucleic acids present on approximately 10000 beads from the 1:1 mixture (sample from before sorting) followed by a digestion with Mlu I and analysis by gel electrophoresis shows, as expected, upon a mixture of Mlu I-susceptible and Mlu I-resistent PCR products (FIG. 13B, lane 6).

When approximately 400 beads collected during the FACS enrichment was subjected to the same analysis, the intensity ratio between the upper band (443 bp, uncleaved) and lower double band (two cleavage products, 239/204 bp, unresolved) had shifted towards the smaller (lower) bands (FIG. 13B, lane 8). Using a Gel Doc 2000 gel scanning instrument and Quantity One vers. 4.1 software (Biorad, Hercules, Calif., USA), this shift in relative intensities were recorded resulting in the overlay plot shown in FIG. 14. From this analysis it can be clearly seen that a shift of the relative intensity towards the lower molecular weight cleavage products had occured. This shows that beads containing Mlu I-susceptible PCR product encoding the FLAG-$Z_{wt}$ fusion protein, had been enriched during the experiment, relative to beads containing the Mlu I-resistent FLAG-$Z_{IgA}$ fusion protein encoding PCR product.

Taken together, this example shows that fusion proteins, here exemplified by the fusion protein FLAG-$Z_{wt}$, can be produced from a corresponding, bead-immobilized, PCR product by cell free transcription/translation, containing a functional affinity fusion partner, here exemplified by the FLAG peptide, which is capable of resulting in a biospecific immobilization of the protein to beads containing a cognate affinity partner, here exemplified by the BioM5 anti-FLAG monoclonal antibody, and that such beads can be enriched when mixed and co-processed with irrelevant beads, containing PCR products encoding a different gene product, by FACS-based enrichment using a suitable combination of detection reagents, here exemplified by a rabbit anti-DNP IgG-HRP conjugate and a signal amplification mixture containing fluorescein tyramide.

What is claimed is:

1. A method for the selection of one or more desired polypeptides comprising:
   (a) providing a solid support having immobilized nucleic acid molecules thereon, the solid support comprising a binding molecule capable of interacting with at least the desired polypeptide or a molecule attached thereto;
   (b) producing polypeptides from said immobilized nucleic acid molecules by cell free expression, said desired polypeptides interacting with said binding molecule;
   (c) isolating the solid support carrying both the desired polypeptide and the nucleic acid encoding it; and optionally
   (d) recovering said nucleic acid and/or said desired polypeptide.

2. A method as claimed in claim 1 wherein the expressed polypeptides are fusion proteins.

3. A method as claimed in claim 2 wherein each fusion protein comprise a variable portion and a common portion.

4. A method as claimed in claim 3 wherein the common portion comprises an affinity fusion partner capable of interacting with said binding molecule.

5. A method as claimed in claim 3 wherein the common portion comprises a reporter protein moiety.

6. A method as claimed in claim 3 wherein the variable portion is a member of a polypeptide library.

7. A method as claimed in claim 1 wherein steps (a), (b) and (c) are performed iteratively for more than one cycle.

8. A method as claimed in claim 7 wherein steps (a), (b) and (c) are performed between 2 and 20 times.

9. A method as claimed in claim 1 wherein the solid support system is a particle.

10. A method as claimed in claim 1 wherein the binding molecule is a target molecule for the desired polypeptide.

11. A method as claimed in claim 1 wherein the binding molecule is a cognate binding partner for an affinity binding partner which forms a fusion protein with the desired polypeptide.

* * * * *